(12) United States Patent
Brown

(10) Patent No.: US 12,351,788 B2
(45) Date of Patent: Jul. 8, 2025

(54) METHODS AND SYSTEMS FOR CULTURING MICROBIAL AND CELLULAR SEED CULTURES

(71) Applicant: Life Technologies Corporation, Carlsbad, CA (US)

(72) Inventor: Jason D. Brown, Logan, UT (US)

(73) Assignee: Life Technologies Corporation, Carlsbad, CA (US)

(*) Notice: Subject to any disclaimer, the term of this patent is extended or adjusted under 35 U.S.C. 154(b) by 1451 days.

(21) Appl. No.: 16/835,687

(22) Filed: Mar. 31, 2020

(65) Prior Publication Data

US 2020/0296905 A1    Sep. 24, 2020

Related U.S. Application Data

(62) Division of application No. 14/507,548, filed on Oct. 6, 2014, now Pat. No. 10,617,070.

(51) Int. Cl.
| | |
|---|---|
| *C12M 1/00* | (2006.01) |
| *C12M 3/00* | (2006.01) |
| *C12M 3/06* | (2006.01) |
| *A01G 9/02* | (2018.01) |
| *A01H 4/00* | (2006.01) |

(52) U.S. Cl.
CPC ............ *C12M 23/14* (2013.01); *C12M 23/28* (2013.01); *C12M 23/46* (2013.01); *C12M 27/16* (2013.01); *C12M 27/20* (2013.01); *A01G 9/02* (2013.01); *A01H 4/005* (2013.01)

(58) Field of Classification Search
CPC ...... C12M 23/14; C12M 23/28; C12M 23/46; C12M 27/16; C12M 27/20; A01G 9/02; A01H 4/005
See application file for complete search history.

(56) References Cited

U.S. PATENT DOCUMENTS

| 2,327,095 A | 8/1943 | Cleary |
| 3,002,895 A | 10/1961 | Freedman |

(Continued)

FOREIGN PATENT DOCUMENTS

| CN | 102787072 A | 11/2012 |
| CN | 202688333 U | 1/2013 |

(Continued)

OTHER PUBLICATIONS

Soren Werner et al., *Innovative, Non-stirred Bioreactors in Scales from Milliliters up to 1000 Liters for Suspension Cultures of Cells Using Disposable Bags and Container—A Swiss Contribution*, Swiss Biotech, CHIMIA 2010, vol. 65, No. 11, 2010, pp. 819-823.

(Continued)

*Primary Examiner* — Liban M Hassan

(57) ABSTRACT

A method for culturing a microbial or cellular seed culture includes positioning a first flexible bag within a chamber of a first retainer, the first retainer being secured to a mixer table. A culture is produced within a compartment of the flexible bag, the culture comprising a growth media and a microbial or cellular starter culture added thereto. The mixer table is activated so that the culture is mixed within the compartment of the first flexible bag while the microbes or cells of the culture grow, the culture having a maximum volume of less than 10 liters.

17 Claims, 13 Drawing Sheets

(56) References Cited

U.S. PATENT DOCUMENTS

| | | |
|---|---|---|
| 3,601,372 A | 8/1971 | Harmes |
| 4,576,310 A | 3/1986 | Isgar |
| 4,661,455 A | 4/1987 | Hubbard |
| 4,665,035 A | 5/1987 | Tunac |
| 4,713,909 A | 12/1987 | Roper |
| 4,906,577 A | 3/1990 | Armstrong et al. |
| 5,002,890 A | 3/1991 | Morrison |
| 5,057,429 A | 10/1991 | Watanabe et al. |
| 5,135,853 A | 8/1992 | Dziewulski et al. |
| 5,156,328 A | 10/1992 | Wozniacki |
| 5,202,254 A | 4/1993 | Amiot et al. |
| 5,225,346 A | 7/1993 | Matsumiya et al. |
| 5,443,985 A | 8/1995 | Lu et al. |
| 5,593,228 A | 1/1997 | Tannenbaum |
| 5,594,177 A | 1/1997 | Hanse |
| 5,799,830 A | 9/1998 | Carroll |
| 6,190,913 B1 | 2/2001 | Singh |
| 6,908,223 B2 | 6/2005 | Bibbo et al. |
| 7,041,493 B2 | 5/2006 | Rao |
| 7,080,750 B2 | 7/2006 | Wein |
| 7,384,783 B2 | 6/2008 | Kunas et al. |
| 7,487,688 B2 | 2/2009 | Goodwin |
| 7,682,067 B2 | 3/2010 | West et al. |
| 7,879,599 B2 | 2/2011 | Goodwin et al. |
| 7,901,934 B2 | 3/2011 | Kunas et al. |
| 8,016,218 B1 | 9/2011 | Friedman |
| 8,282,267 B2 | 10/2012 | Castillo et al. |
| 8,393,781 B2 | 3/2013 | Manera et al. |
| 8,445,242 B2 | 5/2013 | DiCosimo et al. |
| 8,603,805 B2 | 12/2013 | Goodwin et al. |
| 8,641,314 B2 | 2/2014 | Thacker et al. |
| 9,228,166 B2 * | 1/2016 | Barrett ................ C12M 23/46 |
| 2002/0131654 A1 | 9/2002 | Smith et al. |
| 2002/0155595 A1 | 10/2002 | Adelberg |
| 2005/0087534 A1 | 4/2005 | Harris |
| 2005/0130291 A1 * | 6/2005 | Erhardt ................ C12M 23/26 |
| | | 422/209 |
| 2006/0240546 A1 | 10/2006 | Goodwin et al. |
| 2006/0270036 A1 | 11/2006 | Goodwin et al. |
| 2008/0206862 A1 | 8/2008 | Asgari |
| 2008/0274541 A1 | 11/2008 | Selker et al. |
| 2009/0146032 A1 | 6/2009 | Bettenhausen |
| 2009/0233334 A1 | 9/2009 | Hildinger et al. |
| 2011/0013474 A1 | 1/2011 | Ludwig et al. |
| 2011/0188928 A1 | 8/2011 | West et al. |
| 2011/0198286 A1 | 8/2011 | Niazi |
| 2011/0217690 A1 | 9/2011 | Niazi |
| 2011/0217767 A1 | 9/2011 | Niazi |
| 2011/0310696 A1 | 12/2011 | Goodwin et al. |
| 2012/0027324 A1 | 2/2012 | Morrissey et al. |
| 2012/0282688 A1 | 11/2012 | Knight et al. |
| 2012/0329151 A1 | 12/2012 | Baskar et al. |
| 2013/0081995 A1 | 4/2013 | Larsen |
| 2013/0089925 A1 | 4/2013 | Damren et al. |
| 2013/0121103 A1 | 5/2013 | Castillo et al. |
| 2013/0157355 A1 | 6/2013 | Barrett et al. |
| 2013/0316396 A1 | 11/2013 | Fricking |
| 2015/0138913 A1 | 5/2015 | Jones et al. |
| 2016/0095279 A1 | 4/2016 | Brown |
| 2016/0100536 A1 | 4/2016 | Wu |
| 2017/0159001 A1 | 6/2017 | Roell |

FOREIGN PATENT DOCUMENTS

| | | |
|---|---|---|
| EP | 1 442 785 A1 | 8/2002 |
| EP | 1 961 806 A2 | 8/2008 |
| EP | 2 020 433 A2 | 2/2009 |
| EP | 2 336 051 A1 | 6/2011 |
| EP | 2 386 351 A2 | 11/2011 |
| GB | 371441 A | 4/1932 |
| GB | 671683 A | 5/1952 |
| WO | 2000/66706 A1 | 11/2000 |
| WO | 2008/088371 A2 | 7/2008 |
| WO | 2009/114442 A1 | 9/2009 |
| WO | 2012/128703 A1 | 9/2012 |

OTHER PUBLICATIONS

Sartorius stedim biotech, *CultiBag ORB Brochure, Version* 4, 2014.

E.A. Falch et al., *Disposable Shaker Flasks*, Biotechnology and Bioengineering, vol. V, 1963, pp. 211-220.

Jay Kybal et al., *A Device for Cultivation of Plant and Animal Cells*, Biotechnology Letters, vol. 7, No. 7, 1985, pp. 467-470.

International Search Report dated Nov. 12, 2015, issued in PCT Application No. PCT/US2015/051590, filed Sep. 23, 2015.

* cited by examiner

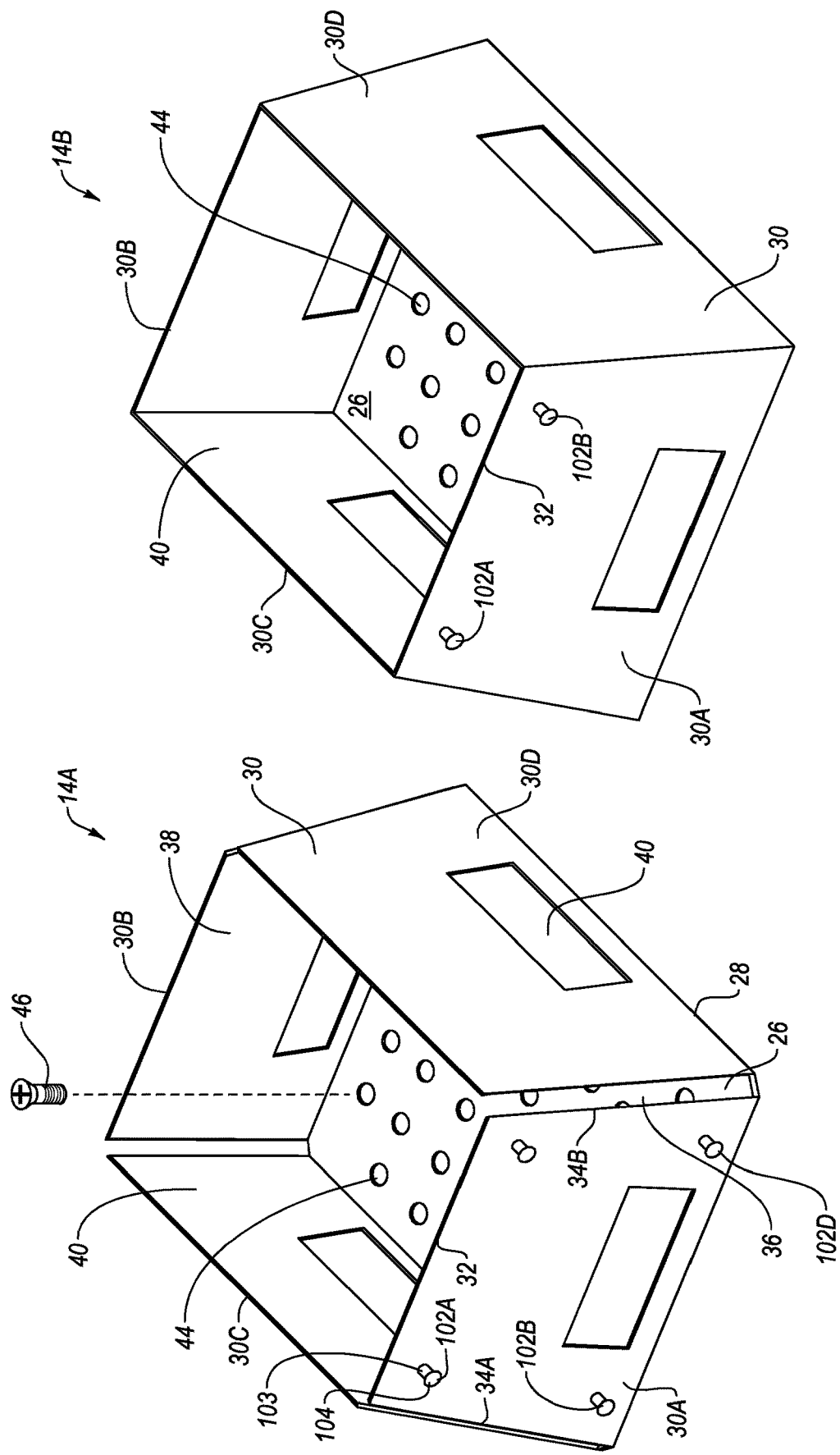

METHODS AND SYSTEMS FOR CULTURING MICROBIAL AND CELLULAR SEED CULTURES

CROSS-REFERENCE TO RELATED APPLICATIONS

This application is a continuation of U.S. application Ser. No. 14/507,548, filed Oct. 6, 2014, which is incorporated herein by specific reference.

BACKGROUND OF THE INVENTION

1. The Field of the Invention

The present invention relates to methods and systems for culturing microbial and cellular seed cultures using disposable container assemblies.

2. The Relevant Technology

The growth of biological cells within a bioreactor requires critical control over a number of different process parameters. For example, as cells grow, they absorb oxygen from the surrounding media and release $CO_2$. The concentration of oxygen and $CO_2$ within the media must be carefully monitored and regulated to ensure viability and optimal growth of the cells. Another factor that needs to be carefully monitored and controlled is the density of the cells within the culture. To make sure that all of the processing parameters are properly controlled, cells are typically grown in sequential stages of increasingly larger reactors. For example, a cellular seed culture may initially start by being grown in a small glass flask which is positioned on a shaker table. Once the cell density approaches a critical value, the culture is transferred to a larger bench top reactor where the culture is combined with additional media.

Although glass flasks are useful in growing a seed culture, they have some shortcomings. For example, between each use it is necessary to clean and sterilize the flask. This process is time consuming, labor intensive and requires the use of chemicals. Furthermore, because of potential failures in the cleaning process, this process has has an increased risk that the cell culture may be contaminated.

Glass flasks also take a large area to transport and store, are prone to breaking, are cumbersome to make sterile gas and fluid connections therewith, can be difficult to remove samples from in a sterile manner, and are not easily operated with multiple sensors.

Accordingly, what is needed in the art are systems and methods for growing cellular seed cultures that address all or some of the above shortcomings.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 2 is a perspective view of a retainer of the system shown in FIG. 1;

FIG. 3 is a perspective view of an alternative embodiment of the retainer shown in FIG. 2;

DETAILED DESCRIPTION OF THE PREFERRED EMBODIMENTS

Figure 1:
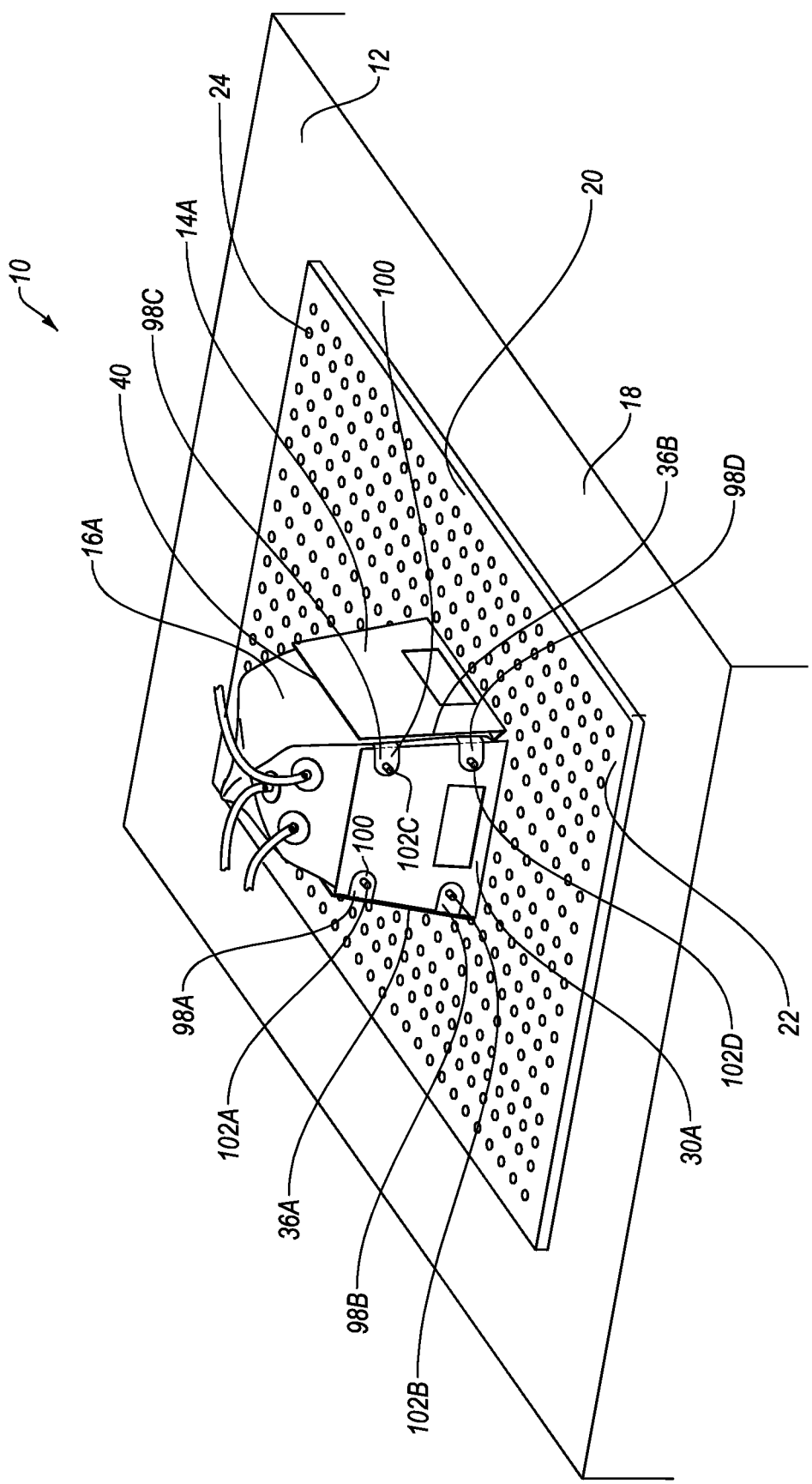
FIG. 1 is a perspective view of a seed culturing system incorporating features of the present invention.

The present invention is directed to methods and systems for culturing microbial or cellular seed cultures. For example, the inventive methods and systems can be used in culturing bacteria, fungi, algae, plant cells, mammalian cells, animal cells, insect cells, plant cells, protozoan, nematodes, and the like from a starter culture.

Before describing the present disclosure in detail, it is to be understood that this disclosure is not limited to particularly exemplified apparatus, systems, methods, or process parameters that may, of course, vary. It is also to be understood that the terminology used herein is only for the purpose of describing particular embodiments of the present invention, and is not intended to limit the scope of the invention in any manner.

All publications, patents, and patent applications cited herein, whether supra or infra, are hereby incorporated by reference in their entirety to the same extent as if each individual publication, patent, or patent application was specifically and individually indicated to be incorporated by reference.

The term "comprising" which is synonymous with "including," "containing," or "characterized by," is inclusive or open-ended and does not exclude additional, unrecited elements or method steps.

It will be noted that, as used in this specification and the appended claims, the singular forms "a," "an" and "the" include plural referents unless the content clearly dictates otherwise. Thus, for example, reference to a "container assembly" can include one, two, or more container assemblies.

As used in the specification and appended claims, directional terms, such as "top," "bottom," "left," "right," "up," "down," "upper," "lower," "proximal," "distal" and the like are used herein solely to indicate relative directions and are not otherwise intended to limit the scope of the invention or claims.

Where possible, like numbering of elements have been used in various figures. Furthermore, multiple instances of an element and or sub-elements of a parent element may each include separate letters appended to the element number. For example two instances of a particular element "91" may be labeled as "91A" and "91B". In that case, the element label may be used without an appended letter (e.g., "91") to generally refer to instances of the element or any one of the elements. Element labels including an appended letter (e.g., "91A") can be used to refer to a specific instance of the element or to distinguish or draw attention to multiple uses of the element. Furthermore, an element label with an appended letter can be used to designate an alternative design, structure, function, implementation, and/or embodiment of an element or feature without an appended letter. Likewise, an element label with an appended letter can be used to indicate a sub-element of a parent element. For instance, an element "12" can comprise sub-elements "12A" and "12B."

Various aspects of the present devices and systems may be illustrated by describing components that are coupled, attached, and/or joined together. As used herein, the terms "coupled", "attached", and/or "joined" are used to indicate either a direct connection between two components or, where appropriate, an indirect connection to one another through intervening or intermediate components. In contrast, when a component is referred to as being "directly coupled", "directly attached", and/or "directly joined" to another component, there are no intervening elements present. Furthermore, as used herein, the terms "connection," "connected," and the like do not necessarily imply direct contact between the two or more elements.

Various aspects of the present devices, systems, and methods may be illustrated with reference to one or more exemplary embodiments. As used herein, the term "exemplary" means "serving as an example, instance, or illustration," and should not necessarily be construed as preferred or advantageous over other embodiments disclosed herein.

Unless defined otherwise, all technical and scientific terms used herein have the same meaning as commonly understood by one of ordinary skill in the art to which the present disclosure pertains. Although a number of methods and materials similar or equivalent to those described herein can be used in the practice of the present disclosure, the preferred materials and methods are described herein.

In certain embodiments, the inventive systems (or portion(s) thereof) are designed so that at least some components that contact the material being processed can be disposed of after each use. As a result, some embodiments of the present invention substantially eliminate the burden of cleaning and sterilization required by conventional glass or plastic systems. This feature also ensures that sterility can be consistently maintained during repeated processing of multiple batches. In view of the foregoing, and the fact that certain embodiments can be easily scalable, relatively low cost, and easily operated, some embodiments of the present invention can be used in a variety of industrial and research facilities that previously outsourced such processing.

Depicted in FIG. 1 is one embodiment of a culturing system 10 incorporating features of the present invention. In general, culturing system 10 comprises a mixer table 12, one or more retainers 14 disposed on mixer table 12, and a container assembly 16 at least partially disposed within each retainer 14. Each of the elements will now be discussed below in greater detail.

Mixer table 12 comprises a base 18 having a platform 20 moveably mounted thereon. Platform 20 has a top surface 22 that is typically flat and disposed in a horizontal plane. Other contours, orientations and configurations can also be used. Although not required, in one embodiment a plurality of threaded holes 24 are uniformly formed over the entire area or a predefined area of top surface 22. Holes 24 typically have a diameter in a range between about 0.2 cm to about 1 cm with about 0.2 cm to about 0.5 cm being more common. Other dimensions can also be used. As will be discussed below in greater detail, in one embodiment, holes 24 are used to secure each retainer 14 to platform 20 at a desired location. The number of holes 24 can depend on the size of platform 20 but a common platform 20 will often include more than 20 holes 24 and typically more than 100, 200 or 400 holes 24. Other numbers can also be used.

Mixer table 12 has a drive motor or other mechanism that facilitates rapid displacement of platform 20 relative to base 18. The displacement can be in a variety of different patterns but commonly results in platform 20 being moved within a single plane. For example, platform 20 can reciprocally move horizontally side-to-side, front-to-back, or combinations of the foregoing. Furthermore, platform 20 can move in a two-dimensional path such as circular path, elliptical path, or other random or repeating path. In other embodiments, platform 20 can be configured to rock or tilt back and forth or can be configured to move in a three dimensional path. For example, platform 20 can rock, tilt or be repeatedly raised and lowered while it is concurrently being moved horizontally such as discussed above. In view of the foregoing, mixer table 12 can comprise a conventional shaker table or rocker table.

Depicted in FIG. 1 is one embodiment of a retainer 14A used for securing container assembly 16 to moveable platform 20. As depicted in FIG. 2, retainer 14A comprises a floor 26 having a perimeter edge 28. Floor 26 has a square or rectangular configuration. However, other configurations can also be used including circular, oval, and other polygonal or irregular configurations. Upstanding from floor 26, typically at perimeter edge 28, are a plurality of sidewalls 30. In the depicted embodiment the plurality of sidewalls 30 include a front sidewall 30A, a rear sidewall 30B, and opposing lateral sidewalls 30C and 30D. Sidewalls 30 are depicted as upstanding from floor 26 and are also inwardly inclined towards floor 26. Specifically, with floor 26 disposed in a horizontal position, sidewalls 30 can commonly incline back towards floor 26 at an angle in a range between about 2° to about 15° with about 3° to about 10° being more common. Other angles can also be used. The sloping of sidewalls 30 is not critical but assists in helping to retain container assembly 16 within retainer 14 and to maintain container assembly 16 in its preferred orientation. In alternative embodiments, sidewalls 30 can extend vertically or could slope outward away from floor 26.

Each sidewall 30 has a top edge 32 that extends between opposing side edges 34A and B. A slot 36 is formed between each adjacent pair of side edges 34 of adjacent sidewalls 30. In the depicted embodiment, slots 36 extend the entire length of side edges 34 from top edge 32 to floor 26. However, slots 36 need not extend to floor 26 and need not extend to top edge 32. For example, sidewalls 30 could bridge slot 36 at top edge 32, adjacent to floor 26 or at one or more locations therebetween so that slots 36 form one or more bounded openings. The function of slots 36 will be discussed below.

Retainer 14A has an interior surface 38 that partially bounds a chamber 40. That is, chamber 40 is at least partially bound by the interior surface of floor 26 and the interior surface of each of sidewalls 30. Chamber 40 is sized to receive container assembly 16. Extending through each sidewall 30 is a window 42 which permits visual inspection of container assembly 16 and which enables a port extending from container assembly 16 to pass therethrough. Windows are not necessary and can be eliminated. Extending through floor 26 are a plurality of spaced apart holes 44. Holes 44 have a size and spacing comparable to holes 24 on platform 20 (FIG. 1). Accordingly, to secure retainer 14 to platform 20, floor 26 of retainer 14 is place on top surface 22 of platform 20 so that at least some of holes 44 are aligned with holes 24. One or more fasteners 46 are then passed through select holes 44 and threaded into holes 24, thereby securing retainer 14 to platform 20. This mechanism for attachment makes it easy to move retainer 14A to any desired location upon platform 20 and makes it easy to attach any number of retainers 14A to platform 20 at any desired position and/or orientation. In alternative embodiments, however, it is appreciated that holes 24 and/or 44 could be replaced with clamps, brackets, straps, and other types of fasteners that permit retainers 14 to be removably secured to platform 20. In other embodiments, one or more retainers 14 can be permanently secured to platform 20, such as by welding or an adhesive. Retainers 14 disclosed herein are common made out of a metal, such as stainless steel or aluminum, but could also be made from plastic, composite, or other materials that will withstand the applied forces.

Depicted in FIG. 3 is an alternative embodiment of a retainer 14B. Like elements between retainers 14A and 14B are identified by like reference characters. Retainer 14B is substantially identical to retainer 14A except that slots 36 have been removed so that sidewalls 30A-D combined to form a continuous sidewall 30 that encircles chamber 40. Again in this depicted embodiment, floor 26 has four sides and four sidewalls 30A-D upstanding therefrom. In alternative embodiments, retainers 14 can be formed with floor 26 having three, five, six, seven, eight, or more sides with a corresponding number of sidewalls upstanding therefrom. The sidewalls can be connected together or have slot(s) formed therebetween. In other embodiments, floor 26 could be circular, oval, or irregular and could thus have a complimentary circular, oval, or irregular sidewall, i.e., a single continuous sidewall, upstanding therefrom. Again, the one or more sidewalls can be vertical or slope inward. For example, a circular sidewall 30 of a retainer 14 could form a frustum of a cone, a cylinder, or other three dimensional configurations that bound chamber 40.

Figure 4:
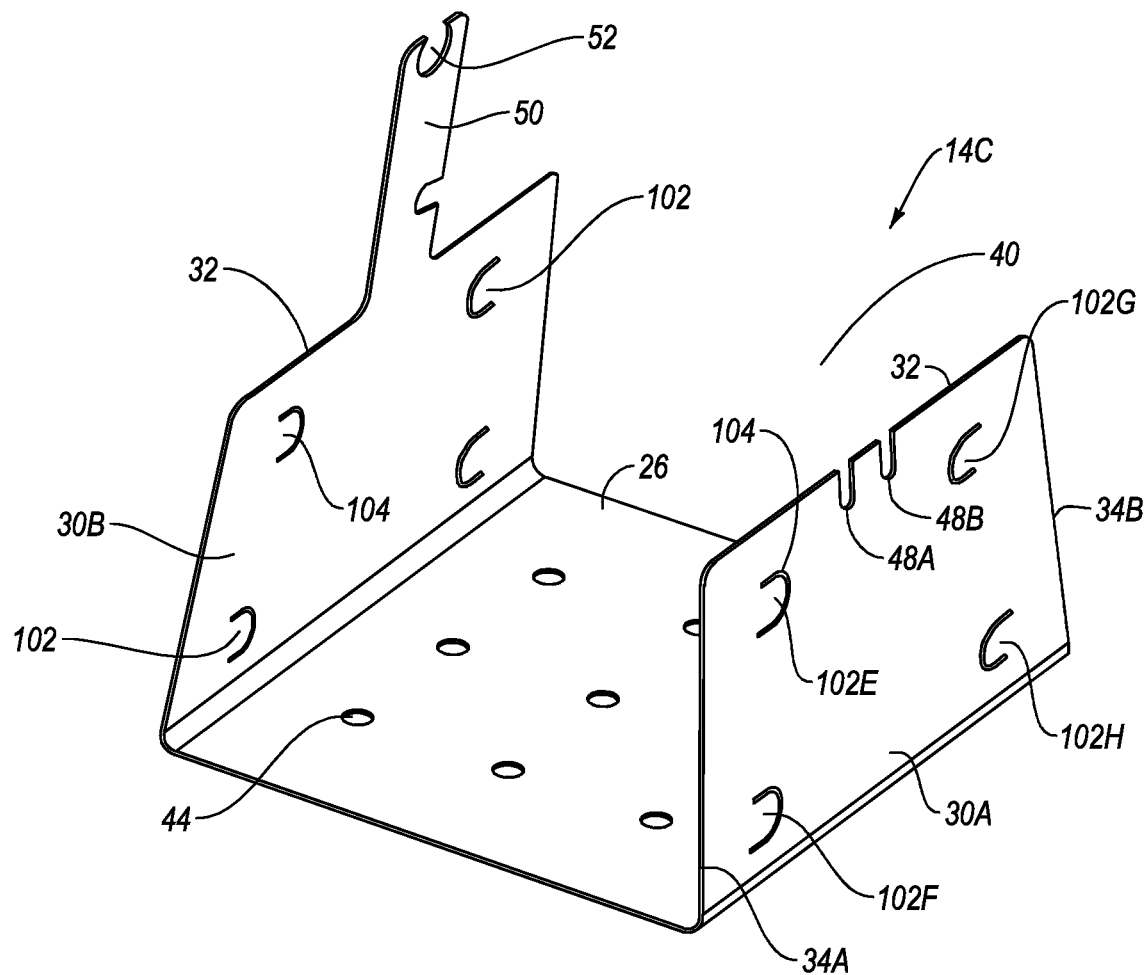
FIG. 4 is a perspective view of another alternative embodiment of a retainer that is formed without lateral sidewalls.

Depicted in FIG. 4 is another alternative embodiment of a retainer 14C. Again, like elements between retainers 14A and 14C are identified by like reference characters. Retainer 14C incudes floor 26 having front wall 30A and opposing rear wall 30B. However, lateral sidewalls 30C and 30D have been eliminated so that chamber 40 is only bounded between sidewalls 30A and 30B. Recessed on top edge 32 of front wall 30A are a pair of grooves 48A and B in which tubes from container assembly 16 can be received and secured by friction fit for desired alignment. Any desired number of grooves 48 can be formed. Upstanding from top edge 32 of rear sidewall 30B is a stand 50 having groove 52 received thereon for engaging and supporting a filter or tube from a container assembly 16.

Figure 5:
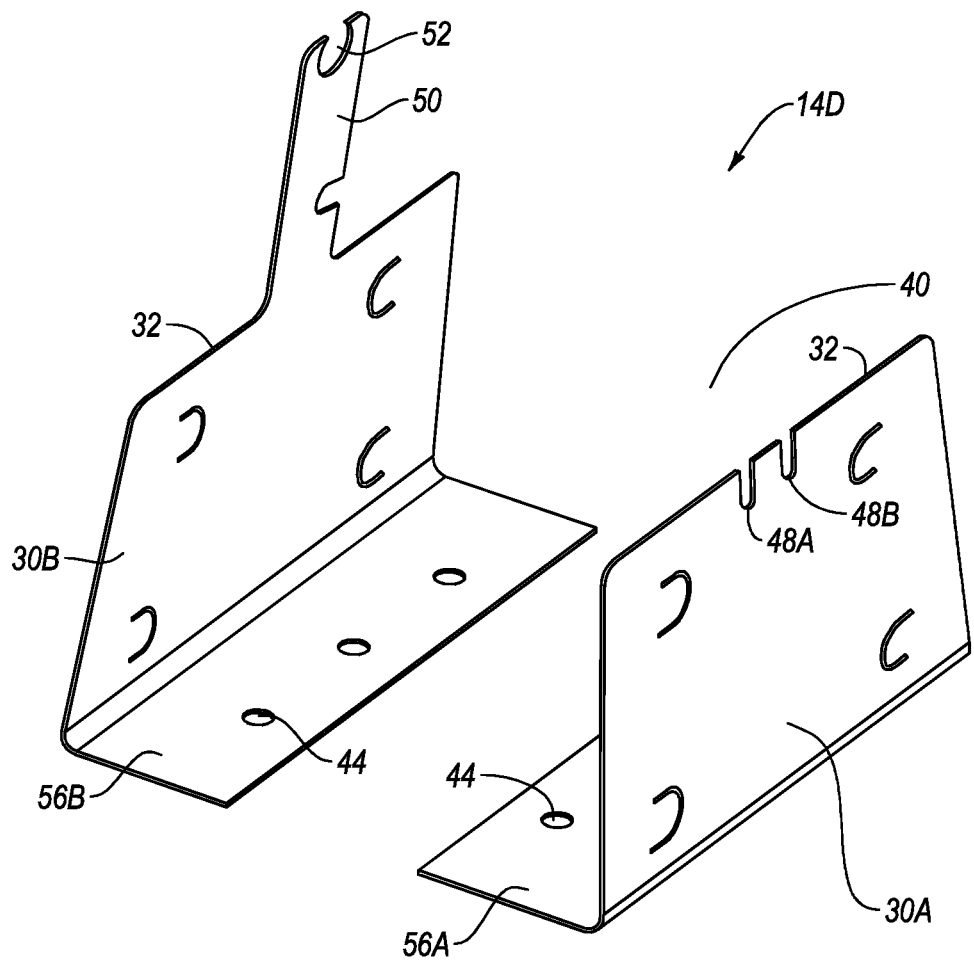
FIG. 5 is a perspective view of yet another alternative embodiment of a retainer wherein the front and rear sidewalls are disconnected from each other.

Depicted in FIG. 5 is still another alternative embodiment of a retainer 14D incorporating features of the present invention. Again, like elements between retainer 14A and 14D are identified by like reference characters. Retainer 14D incudes front sidewall 30A and rear sidewall 30B. However, in contrast to the sidewalls being connected together by a single continuous floor 26 extending therebetween, each sidewall 30A and 30B has a separate floor portion 56A and B, respectively, from which sidewalls 30A and 30B upstand. Holes 44 extend through each floor portion 56 to enable floor portions 56 to be selectively attached to platform 20, as previously discussed, at a preferred spacing and orientation so that chamber 40 is formed between sidewalls 30A and 30B. It is appreciated that any number of separate sidewalls 30 having a separate floor portion 56 connected thereto can be separately mounted to platform 20 for forming the desired chamber 40.

With regard to each of the above retainers 14A-14C, it is appreciated that examples, materials, and alternative embodiments discussed for one are also applicable to the others and that features between the different retainers can be mixed and matched to form other retainers. Furthermore, other retainers not disclosed herein but that can support a container assembly 16 on platform 20 can also be used.

As depicted in FIG. 1, container assembly 16A is positioned within chamber 40 of retainer 14A so that retainer 14A holds container assembly 16A on platform 20 as platform 20 moves. In general, container assembly 12 is configured to hold a culture which includes a starter culture and growth media. Mixer table 12 rapidly moves container assembly 12 so that the culture is continuously uniformly mixed. Gas delivered into container assembly 12 interacts with the culture to oxygenate the culture. Depending on the application, the gas can also be used to strip $CO_2$, regulate the pH and have other purposes. The culture typically continues to grow within container assembly 12 until the culture achieves a desired cell/microorganism density. The culture is then transferred to a larger container for subsequent growth and processing.

Figure 6:
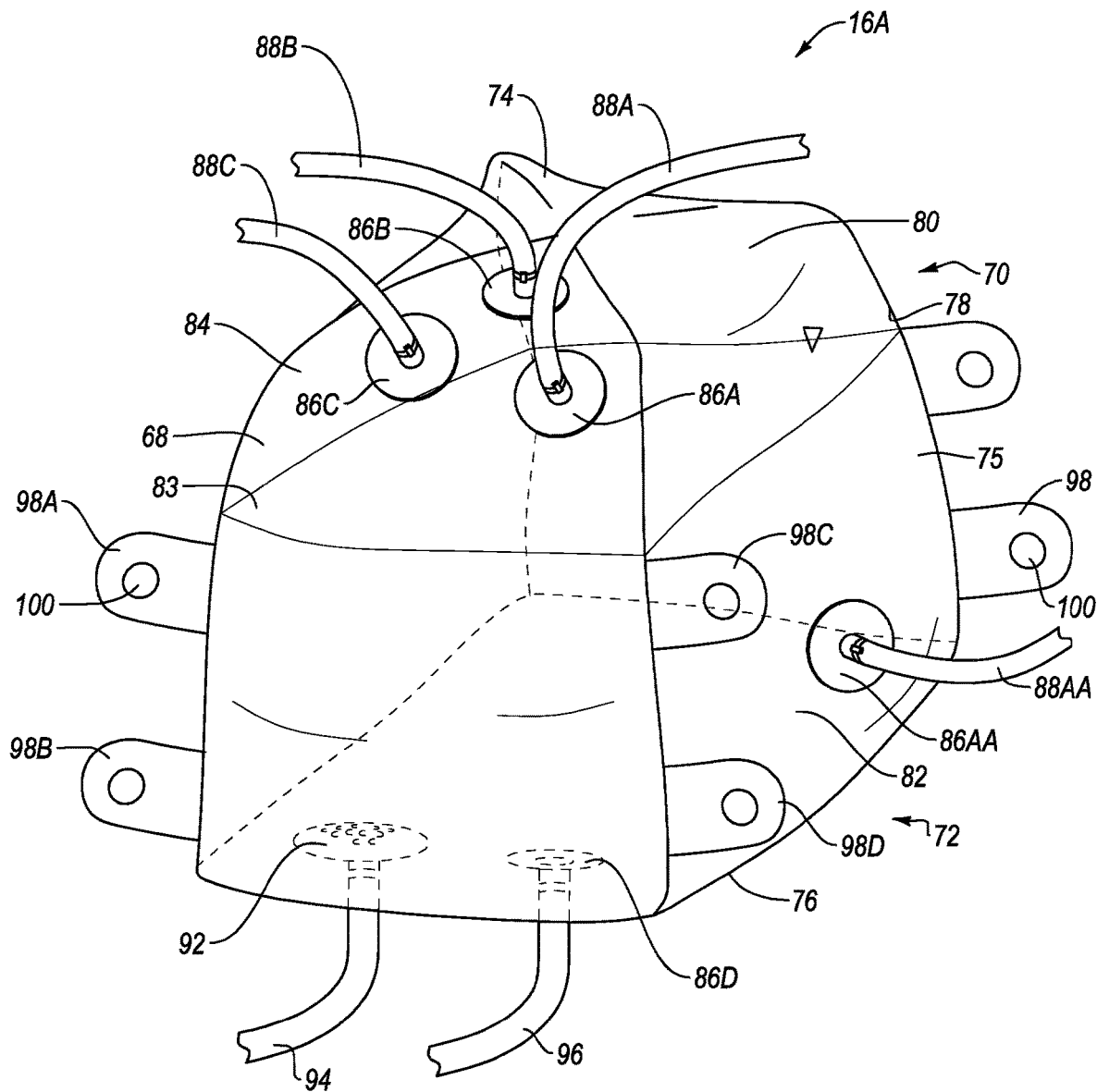
FIG. 6 is a perspective view of the container assembly of the system shown in FIG. 1.

Turing to FIG. 6, container assembly 16A comprises a flexible bag 68 having an upper end 70 to an opposing lower end 72. Upper end 70 can terminate at an upper end wall 74 while lower end 72 can terminate at a lower end wall 76. An encircling sidewall 75 can extend between end walls 74 and 76. Flexible bag 68 also has an interior surface 78 that bounds a compartment 80. Compartment 80 is configured to hold a fluid such as a biological culture. In the depicted embodiment, a culture 82 is shown housed within compartment 80 having a top surface 83. A head space 84 occupies the remainder of compartment 80 above top surface 83 of culture 82.

Culture 82 comprises a starter culture and a growth media. The starter culture comprises cells or microorganisms that are used to inoculate the growth media. The starter culture can comprise a colony of cells or microorganisms from a new line of cells or microorganisms or can be taken from an existing culture of cells or microorganisms. The starter culture can be in a frozen or at least partially frozen state, in a free flowing liquid state, or in a semi-sold state such as a colony growing on an agar plate. The starter culture typically has a volume in a range between about 0.25% to about 20% of the total culture volume with between about 1% to about 10%, about 1% to about 5% or about 5% to about 10% of the total culture volume being more common. Other percentages can also be used. As is known in the art, the growth media comprises a media broth which can be mixed with nutrients, vitamins, and/or other desired components to optimize the desired growth of the starter culture. Culture 82 comprising the combination of the starter culture and the growth media and typically has a volume in a range between 0.3 liters about to about 10 liters with between about 1 liter to about 7 liters or about 1 liter to about 5 liters being more common. The volume of culture 82 is often less than 10 liters, 7 liters, 5 liters or 3 liters. Other volumes can also be used.

Continuing with FIG. 6, flexible bag 68 is comprised of a flexible, water impermeable material such as a low-density polyethylene or other polymeric sheets or film having a thickness in a range between about 0.05 mm to about 5 mm with about 0.1 mm to about 1 mm being more common. Other thicknesses can also be used. The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive. Examples of extruded material that can be used in the present invention include the HyQ CX3-9 and HyQ CX5-14 films available from Life Technologies Corporation out of Logan, Utah. The material can be approved for direct contact with living cells and be capable of maintaining a solution sterile. In such an embodiment, the material can also be sterilizable such as by ionizing radiation. Prior to use, container assembly 16A is typically sealed closed and sterilized so that compartment 80 is sterile prior to the introduction of a seed culture.

In one embodiment, flexible bag 68 can comprise a two-dimensional pillow style bag. In another embodiment, flexible bag 68 can be formed from a continuous tubular extrusion of polymeric material that is cut to length. The ends can be seamed closed or panels can be sealed over the open ends to form a three-dimensional bag. Three-dimensional bags not only have an annular sidewall but also a two dimensional top end wall and a two dimensional bottom end wall. Three dimensional containers can comprise a plurality of discrete panels, typically three or more, and more commonly four or six. Each panel is substantially identical and comprises a portion of the sidewall, top end wall, and bottom end wall of the container. Corresponding perimeter edges of each panel are seamed together. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-0131654 A1, published Sep. 19, 2002, which is incorporated herein by specific reference in its entirety.

It is appreciated that flexible bag 68 can be manufactured to have virtually any desired size, shape, and configuration. Flexible bag 68 is typically formed having a compartment 80 having a volume in a range between 0.5 liters and 15 liters with between 1 liter and 10 liters or between 1 liter and 7 liters being more common. Often the volume of compartment 80 is in a range between 1.1 to 10 times the volume of culture 82 initially formed within compartment 80 with between 1.5 to 6 or 2 to 4 times the volume of culture 82 being more common. Other volumes can also be used. As discussed below, having the volume of compartment 80 be greater than the volume of culture 82 disposed therein is more important when growing cells/microorganisms aerobically than when growing anaerobically. When growing aerobically, the extra volume, i.e., head space 84, is used for holding the gas which oxygenates the cells/microorganisms during mixing of the culture. When growing the cells/microorganisms anaerobically, the gas is not used and thus a large head space 84 is not required. In this embodiment, the tube and port leading to the gas filter can be eliminated or the tube leading the gas filter can be clamped closed.

Although flexible bag 68 can be any shape, in one embodiment flexible bag 68 is configured to rest against the one or more of sidewalls 30 of retainer 14 when received within chamber 40, thereby helping to support container assembly 16 and maintain it in its desired orientation during use.

As also shown in FIG. 6, container assembly 16A further comprises a plurality of ports 86 secured to flexible bag 68 and communicating with compartment 80. Ports 86 can comprise a conventional barbed port, tube port, or any other type of tubular fitting for coupling a tube to flexible bag 68. In the depicted embodiment, three port 86A-C are formed on flexible bag 68 at upper end 70 with tubes 88A-C coupled therewith, respectively. Tubes 88 and other tubes discussed herein can comprise any form of tubular member but typically comprise flexible tubing or hose. Tubes 88 can have a variety of different uses. By way of example and not by limitation, tube 88A can be used for delivering the starter culture and growth media into compartment 80 for forming culture 82. In other embodiments, the starter culture and growth media can be combined to form culture 82 outside of flexible bag 68 and then delivered into compartment 80 through tube 88A. Tube 88A can also be used for removing culture 82 from compartment 80. Tube 88B can be used for delivering a gas into compartment 80. The gas typically comprises air or oxygen and is often mixed with other gases such as nitrogen. Tube 88C can be used for removing gas from compartment 80 or can enable gas to transfer between the surrounding environment and head space 84 by passing through a gas filter. In the depicted embodiment, each of tubes 88A-C communicates directly with head space 84 through ports 86A-C, respectively. In alternative embodiments, as discussed below, one or more of tubes 88 could communicate directly with culture 82 by one or more of ports 86A-C being positioned at lower end 72, lower end wall 76, or sidewall 75.

Any number of tubes 88 can be coupled with flexible bag 68 and each tube can have one or multiple different uses. For example, because flexible bag 68 is relatively small and holds a relatively small amount of fluid, flexible bag 68 can be manually picked up and moved even when filled with a desired volume of culture. Thus, when it is desired to test culture 82 or to remove culture 82 from flexible bag 68, i.e., when culture 82 has achieved a desired cell or microorganism density, flexible bag 68 can be manually lifted and then inverted so that culture 82 passes to one of tubes 88 disposed at upper end 70 or upper end wall 74 such as tube 88A. A syringe can couple with tube 88A and be used to draw out a sample of culture 82 through tube 88A for testing. Alternatively, tube 88A can be coupled with a container and then used to dispense culture 82 into the container under gravity flow. The container could be smaller than flexible bag 68 if only colleting a sample or larger than flexible bag 68 if dispensing for subsequent processing. This coupling with a syringe or other container typically occurs within a sterile hood and container assembly 16 or at least flexible bag 68 and/or tube 88A can be manually moved into the sterile hood during such coupling and dispensing. However, in an alternative embodiment, a drain tube 96 can be coupled with flexible bag 68 at lower end 72 or lower end wall 76 through a port 86D. Drain tube 96 can be used for draining or drawing culture 82 out of compartment 80 without the need for inverting or compressing flexible bag 86. Drain tube 96 could be used while container assembly 16A remains supported on platform 20 or could be used after container assembly 16A is manually removed from platform 20. Likewise, a tube 88AA can be coupled to sidewall 75 of flexible bag 68 through a port 86AA and be used for drawing samples of culture 82 out of flexible bag 68. Tube 88AA can pass through window 40 of retainer 14A (FIG. 2). In other embodiments, a dip tube could be disposed within compartment 80 and coupled with tube 88A. The dip tube could be used for drawing or pushing culture out of compartment 80, such as by compressing flexible bag 68, without the need for inverting container assembly 16.

Because of the relative small volume of culture 82 within flexible bag 68, it is typically not necessary to use a sparger disposed at lower end 72 of flexible bag 68 for delivering gas into compartment 80. That is, the gas is typically used for oxygenating the culture, stripping $CO_2$ from the culture and regulating the pH of the culture. In large scale bioreactors and fermenters, this is typically accomplished by continuously delivering a gas at the bottom of the container so that the gas passes up through the culture in small and/or large bubbles accomplishing a mass transfer between the culture and the gas before the gas enters the head space in the container. An impeller or other mixing element is typically used to concurrently mix the culture so that the mass transfer occurs throughout the culture. As used herein, the term "sparger" is intended to broadly cover fritted, porous, perforated and other gas permeable structures through which gas can be passed to disperse small bubbles of gas into a liquid and also includes pipes, tubes, ports and other structures that can be used to deliver larger bubbles into a liquid.

In one embodiment of the present invention, gas can be fed into compartment 80 through tube 88B, or other tube 88, so that gas enters directly into headspace 84 in compartment 80 without passing through culture 82. Furthermore, in contrast to continuously delivering gas into compartment 80 under a forced gas flow or positive gas pressure during the growth of phase of culture 82, because culture 82 is a relatively small volume and is only grown within container assembly 16 for a relatively short time period, the gas can be delivered to fill or sufficiently fill head space 84 at the start of the growth phase but not be subsequently delivered under a forced gas flow or positive gas pressure during the subsequent growth phase. Mixing culture 82 within compartment 80 through the use of mixer table 12 is sufficient to cause homogeneous mixing of culture 82 and to achieve sufficient mass transfer between culture 82 and the gas within head space 84 without the need for an applied forced gas flow or positive gas pressure. However, a filter, such as filter 120 depicted in FIG. 8 and discussed below, can be mounted on the end of tube 88C. During the growth phase, air can freely transfer between the surrounding environment and compartment 80 by passing through filter 120 to assist in maintaining the desired oxygenation of culture 82.

Accordingly, in one embodiment of the present invention where flexible bag 68 is filled with gas prior to delivery of the starter culture, culture 82 can be grown in flexible bag 68 without supplying a forced flow of gas into flexible bag 68 during growth of culture 82 therein. Alternatively, where the starter culture is delivered into flexible bag 68 prior to filling flexible bag 68 with a gas, culture 82 can be grown in flexible bag 68 by supplying a forced flow of gas into the compartment of the flexible bag 68, during growth of culture 82, for a period of time that is less than 15% and more commonly less than 10%, 5% or 1% of the total time period that culture 82 is grown within flexible bag 68.

Again, sufficient mass transfer between the gas and culture 82 can be achieved in the manner discussed above because of the relatively small volume of culture 82 that is being treated and the relatively short growth period. As such, in one embodiment of the present invention, container assembly 16 is void of any sparger located at lower end 72 of flexible bag 68 which could dispense gas bubbles directly into the culture 82 within compartment 80. Likewise, container assembly 16 can also be void of any mixing element within compartment 80 that is configured to directly mix culture 82 within compartment 80 by movement of the mixing element within compartment 80. Such mixing elements could include an impeller, paddle, stir bar, or other elements that can achieve mixing by having a driven movement, e.g., driven by a rotating drive shaft, reciprocating shaft, magnetic mixer or other mechanism that engages with the mixing element.

Avoiding the use of a sparger and mixing element simplifies the manufacture, use and operation of container assembly 16 and decreases manufacturing and operation costs. For example, by having all tubes 88 connect at upper end 70 of flexible bag 68, container assembly 16A can be easily positioned within chamber 40 of retainer 14 without tubes 88 interfering with retainer 14, without the need to modify retainer 14 or mixer table 12 to receive one or more tubes 88 and without the risk of one or more tubes 88 being kinked or pinched.

In an alternative embodiment and use, however, as depicted in FIG. 6, a sparger 92 coupled with a gas line 94 can be coupled with flexible bag 68 at lower end 72 or lower end wall 76 so that gas passing out of sparger directly enters into and is required to pass through a portion of culture 82 before reaching head space 84. The gas can be delivered continuously through sparger 92 or can be delivered continuously directly into head space 84 through a tube 88 during the growth phase of culture 82. Furthermore, independent of or in conjunction with sparger 92, a mixing element having a driven movement could be disposed within compartment 80 for mixing culture 82 therein.

In large volume bioreactors and fermenters where a culture is grown for an extended period of time, it is critical that the chemical and physical properties of the culture be continuously monitored and regulated to maintain the viability of the culture. To that end, sensor such as dissolved oxygen sensors, pH sensors, temperature sensor, carbon dioxide sensors, cell mass sensors, nutrient sensors and the like and combinations of the foregoing are disposed within and/or coupled to the container of conventional bioreactors and fermenters to sense the chemical and physical properties of the culture therein.

In contrast, because the present invention is directed to the initial growth of a starter culture which is relatively small and is grown over a relatively short period of time before being transferred to a larger container, it is less critical to continuously monitor the physical and chemical properties of the culture. That is, those skilled in the art can safely maintain desired physical and chemical properties of an initial start-up culture without having to continuously monitor the properties through sensors. Where some monitoring is required, periodic samples of culture 82 can be taken and the desired properties measured.

As such, in one embodiment of the present invention, container assembly 16A can be void of any sensors that directly measure the physical or chemical properties of culture 82 within compartment 80. Thus container assembly 16A can be void of any dissolved oxygen sensors, pH sensors, temperature sensors, mass sensors, and/or nutrient sensors that are disposed within, coupled to or interact with container assembly 16A or flexible bag 68 to sense corresponding properties of the culture within compartment 80. This configuration of system 10 simplifies the operation of the system and minimizes costs. In other embodiments, however, one or more of the above sensors can be coupled with or otherwise interact with flexible bag 68 to detect the corresponding properties of the culture within compartment 80. The sensors can be connected to flexible bag 68 through one or more ports mounted on flexible bag 68. Examples of how sensors can be mounted to flexible bag 68 through ports is disclosed in U.S. Pat. No. 7,487,688 issued Feb. 10, 2009 and U.S. Pat. No. 7,901,934 issued Mar. 8, 2011, which are incorporated herein by specific reference.

One of the unique features of one embodiment of the present invention is that because container assembly 16 is formed from polymeric sheets and flexible tubing, container assembly 16 is easy and inexpensive to manufacture. As such, container assembly 16 can be disposed of after a single use. This disposable avoids the need for cleaning and re-sterilization and thereby minimizes any risk of contamination. This is in contrast to conventional glass flasks which must be cleaned and sterilized between each use. Furthermore, in contrast to conventional glass and plastic flasks which occupy a large volume during transport and storage and are prone to breaking, container assembly 16 can be collapsed for transport and storage so as to occupy minimal space and there is minimal risk of breaking.

In one embodiment of the present invention, means are provided for removably securing container assembly 16 to retainer 14. By way of example and not by limitation, as also depicted in FIG. 6, container assembly 16A further comprises a plurality of tabs 98 outwardly projecting from flexible bag 68. Tabs 98 can be made from the same material as flexible bag 68, i.e., polymeric sheet or film, and can be attached to flexible bag 68 by having one end welded or otherwise secured between edges of adjoining sheets forming flexible bag 68. Any desired numbers of tabs 98 can be attached to flexible bag 68. For example, container assembly 68 can have at least two, four, six, eight, ten or more tabs 98 projecting therefrom.

In one embodiment of the present invention, means are provided for securing tabs 98 to retainer 14 which means comprises part of the means for removably securing container assembly 16 to retainer 14. By way of example and not by limitation, each tab 98 is shown having an opening 100 extending therethrough. Returning to FIG. 2, outwardly projecting from exterior surface of front sidewall 30A are a plurality of fasteners 102. Specifically, fasteners 102A and B are disposed adjacent to side edge 34A while fasteners 102C and D and disposed along opposing side edge 34B. Corresponding fasteners also project from the exterior surface of rear sidewall 30B.

During use, as depicted in FIG. 1, container assembly 60A is received within chamber 40. Tabs 98A and B are passed through a slot 36A and folded over fasteners 102A and 102B, respectively, so that fasteners 102A and 102B pass through corresponding openings 100 in tabs 98A and B. Likewise, tabs 98C and D are passed through a slot 38B and folded over fasteners 102C and 102D, respectively, so that fasteners 102C and 102D are received within the openings 100 thereof. Four tabs located on the opposing side of flexible bag 68 are likewise passed through corresponding slots on retainer 14A and engage fasteners 102 projecting from rear sidewall 30B. As a result of the engagement between tabs 98 and fasteners 102, container assembly 16A/flexible bag 68 is secured to retainer 14. This securing between retainer 14 and container assembly 16A helps to prevent container assembly 16A from separating from retainer 14A during movement of mixer table 12 and helps to prevent container assembly 16A from rotating out of proper alignment within chamber 40 of retainer 14A. Furthermore, securing container assembly 16A to retainer 14A helps to optimize mixing of culture 82 within container assembly 16A during movement of mixer table 12.

It is noted that tabs 98A and C are located at upper end 70 of flexible bag 68 while tabs 98B and D are located at lower end 72 of flexible bag 68. Positioning and using tabs 98 at upper end 70 as opposed to just lower end 72 optimizes the retaining of container assembly 16. Alternatively, for smaller flexible bag 68, i.e., typically 6 liters or less, one tab 98 located midway between depicted tabs 98A and B and one tab located midway between tabs 98C and 98D could be sufficient to secure those vertical corners of flexible bag 68. A single tab 98 could likewise be used on the other corners.

In the depicted embodiment, fasteners 102 comprise a linear stem 103 having an enlarged rounded head 104 disposed at the free end thereof. In alternative embodiments, fasteners 102 could be in the shape of hooks, elbows, curved arms or other projections that are configured to be received within openings 100. In still other embodiments, fasteners 102 could be in the form of screws, bolts, pegs, pins, or the like that pass through openings 100 and thread or otherwise engage with sidewalls 30. In yet other embodiments, openings 100 can be eliminated and the fasteners could comprise clamps, wedges, clips, or other types of fasteners that directly engage tabs 100. In other embodiments, other conventional fasteners such as buckles, Velcro (i.e., hook and loop), snaps, buttons, springs, ties, line and the like could be used to connect tabs 100 to retainer 14 or used to container assembly 16 to retainer 14 without the use of tabs 100. By forming slots 26 through which tabs 98 can pass, container assembly 16A can be secured to retainer 14 at both upper end 70 and lower end 72. However, in the alternative embodiments where slots 26 are not provided, such as in retainer 14B depicted in FIG. 3, fasteners 102 can be disposed adjacent to top edge 32 of sidewall 30. For example, fasteners 102A and 102B are disposed on the exterior surface of front wall 30A adjacent to top edge 32. Tabs 98 at upper end 70 of flexible bag 68 can then pass over top edge 32 and then fold over fasteners 102A and 102B so that the fasteners are received within openings 100 of each tab 98. Again, other fasteners as previously discussed can be used to connect tabs 98 to retainer 14B.

Returning to retainer 14C depicted in FIG. 4, in contrast to fasteners 102 being in the form of cylindrical pegs, retainer 14 has fasteners 102 in the form of rounded projections that are formed by cutting U-shape slots 104 through front sidewall 30A and rear sidewall 30B. Specifically, fasteners 102A and E are formed adjacent to side edge 34A while fasteners 102G and H are formed adjacent to side edge 34B. With container assembly 16A disposed within compartment 40, tabs 98A and B (FIG. 6) can fold around side edge 34A and manipulate so that fastener 102E and F side into openings 100 on tabs 98A and B. Likewise, tabs 98C and D (FIG. 6) can fold around side edge 34B so that fasteners 102G and H slide into openings 100 of tabs 98C and D. Tabs 98 on the back side of container assembly 16A are similarly attached to retainers 102 on rear sidewall 30B. In this configuration, tabs 98 secure container assembly 16A to retainer 14C so that the lateral sidewalls extending between front sidewall 30A and rear sidewall 30B are not required. Again it is appreciated that virtually any type of projection that can be received within opening 100 of a tab 98 can be used as a fastener 102. Likewise, other types of connection can be used to secure container assembly 16A to retainer 14C.

Figure 7:
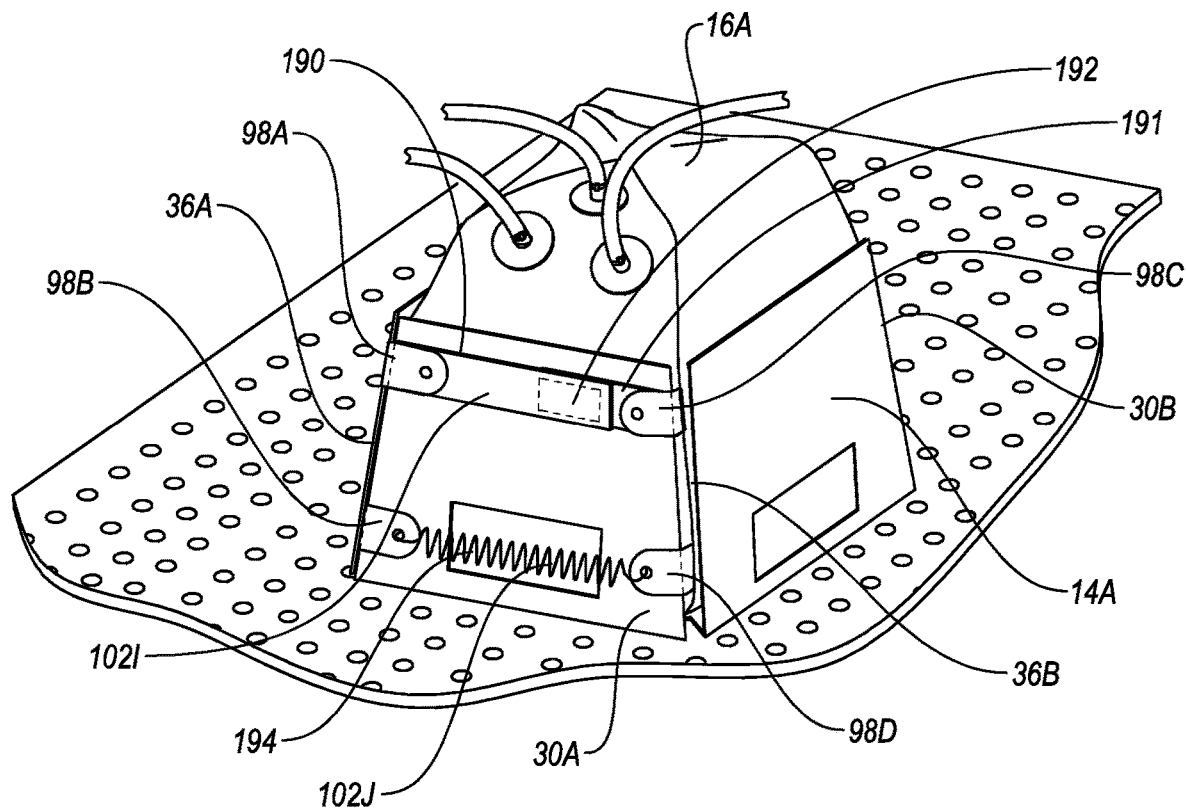
FIG. 7 is a perspective view of a container assembly disposed within the retainer of FIG. 2 wherein opposing tabs of the container assembly are secured together by fasteners.

In another embodiment as depicted in FIG. 7, with tabs 98A and B passed through slot 36A and tabs 98C and D passed through slot 36B, a fastener 102I extends between tabs 98A and C on the outside of front sidewall 30A while a fastener 102J extends between tabs 98B and D on the outside of front sidewall 30A. Although fasteners 102I and J are not secured to retainer 14A, connecting tabs 98 together secures container assembly 16A to retainer 14A. In the embodiment depicted, fastener 102I comprises a first strap 190 that is secured to tab 98A and a second strap 191 that is secured to tab 98C. Straps 190 and 191 are removably secured together by a fastener 192 such as hook and loop (Velcro), snaps, hook, buckle, clamp or the like. In another embodiment, straps 190 and 191 can form one continuous strap that is looped through tabs 98A and C with the opposing ends connected together by fastener 192. To illustrate a further contrasting example, fastener 102J comprises a spring 194 having opposing ends connected to tabs 98B and D. Those skilled in the art will appreciate that a variety of different types of fasteners such as straps, cinches, lines and the like could be used to replace fastener 102H and/or I that secure tabs 98 together.

Fasteners 102I and J can also be used to secure together opposing tabs 98 on the outside of rear sidewall 30B. Fasteners 102I and J are particularly well suited for connecting container assembly 16 to retainers 14C and 14D depicted in FIGS. 4 and 5, respectively, where the retainers do not include lateral sidewalls 30C and D.

Figure 8:
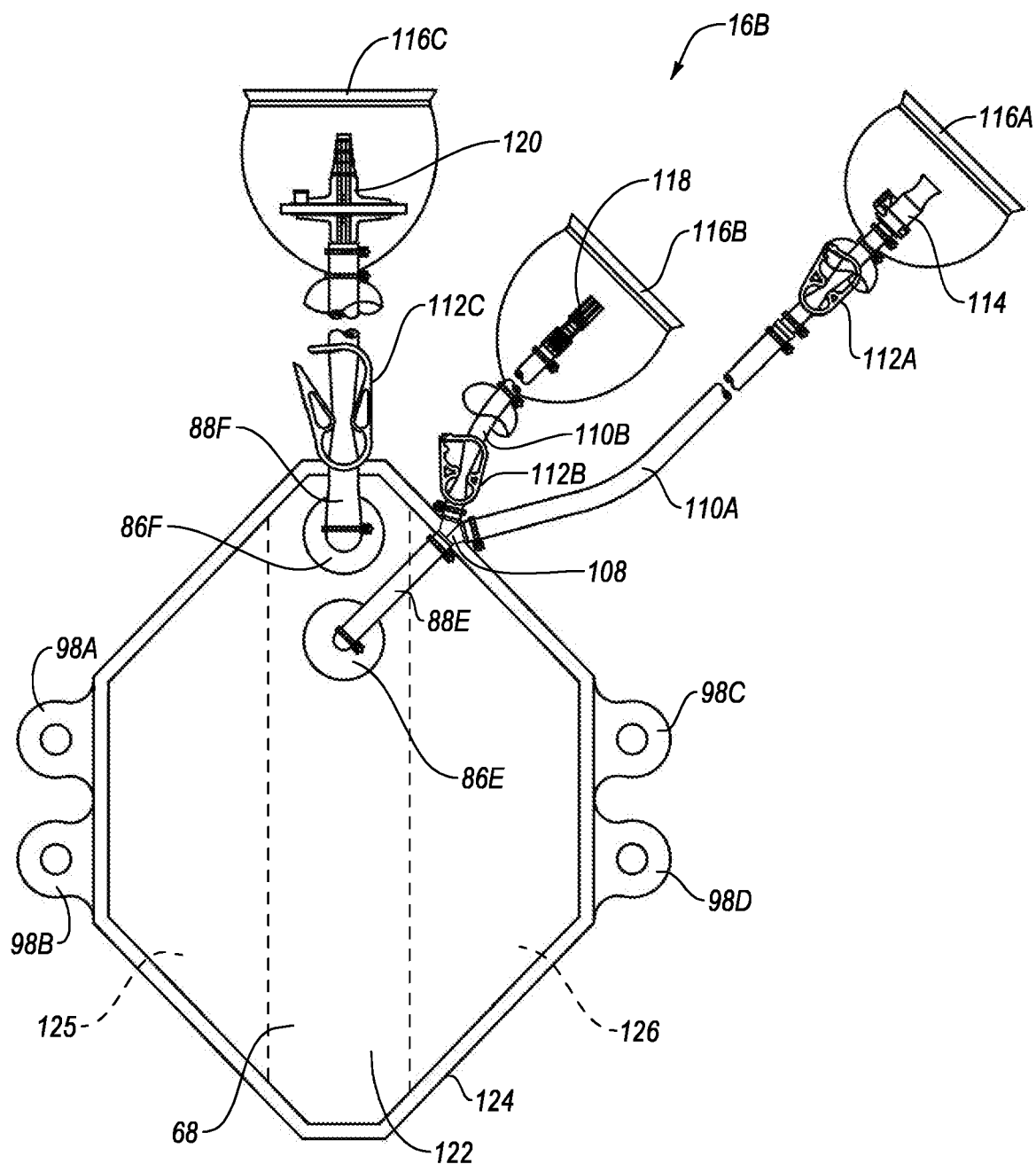
FIG. 8 is a perspective view of an alternative embodiment of the container assembly shown in FIG. 6.

Depicted in FIG. 8 is an alternative embodiment of a container assembly 16B incorporating features of the present invention. Like elements between container assembly 16A and 16B are identified by like reference characters. Container assembly 16B comprises flexible bag 68 depicted in a collapsed position. Flexible bag 68 comprises a top sheet 122, an opposing bottom sheet 124 having a complementary configuration and two folded over side sheets 125 and 126 in the form of gussets that are disposed between sheets 122 and 124 along opposing sides thereof. The sheets are welded together along the perimeter edges so that the flexible bag 68 can expand. A tube 88A is coupled with flexible bag 68 by a port 86E. Tube 88A has a Y-connector 108 formed on the end thereof which couples tubes 110A and B to tube 88A. Tube 110A has a clamp 112A which can be opened and closed to selectively open and close the fluid pathway extending through tube 110A. Mounted on the end of tube 110A is a fitting 114 which can be used to selectively couple with a separate container for either delivering fluid into flexible bag 68 or dispensing fluid out of flexible bag 68. A removable cover 116A is disposed over fitting 114 to maintain fitting 114 sterile after container assembly 16B has been sterilized as a fully assembled system. During use, cover 116A is removed within a sterile hood for coupling to the desired container or fluid source.

Tube 110B also has a clamp 112B mounted thereon for selectively opening and closing the pathway extending through tube 110B. A fitting 118 is disposed on the end of tube 110B and is used for coupling with a gas source for delivering a gas into flexible bag 68. As with fitting 114, a cover 116B is removably disposed over fitting 118. A clamp 112C is disposed on tube 88F and is likewise used for selectively opening and closing the passageway through tube 88F. A sterilizing gas filter 120 is disposed on the end of tube 88F. As previously discussed, in one embodiment of use the gas source is merely used to fill head space 84 (FIG. 6) with gas and is then turned off during the growth phase of culture 82. In this case, gas filter 120 prevents the over pressurization of flexible bag 68 during initial filling by allowing gas to escape and also permits the free flow of gas between the environment and head space 84 by allowing gas to pass through filter 120. Filter 120, however, prevents any contaminants in the environment from passing into container 68 through tube 88F. As such, filter 120 can comprise a gas sterilization filter such as a filter having a maximum pore size that is 2 microns or less.

In an alternative method of use, the gas source can be used to deliver a continuous or substantially continuous gas stream to head space 84 during the growth phase of culture 82. For example, the gas can be delivered into the compartment of flexible bag 68, during growth of culture 82, for a period of time that is greater than 70% and more commonly greater than 80% or 90% of the total time period that culture 82 is grown within flexible bag 68. As gas pressure builds up within flexile bag 68, gas can pass through tube 88F and out filter 120 into the surround environment. Filter 120 thus enables gas to safely escape from flexible bag 68 without permitting contaminants in the environment from passing into container 68 through tube 88F.

A removable cover 116C is also disposed over filter 120 which is removed prior to use. In view of the foregoing, it is appreciated that a variety of different tube configurations and fittings can be used on each container assembly 16B. In this embodiment, it is noted that no tubes or spargers are disposed at the lower end of flexible container 68.

Figure 9:
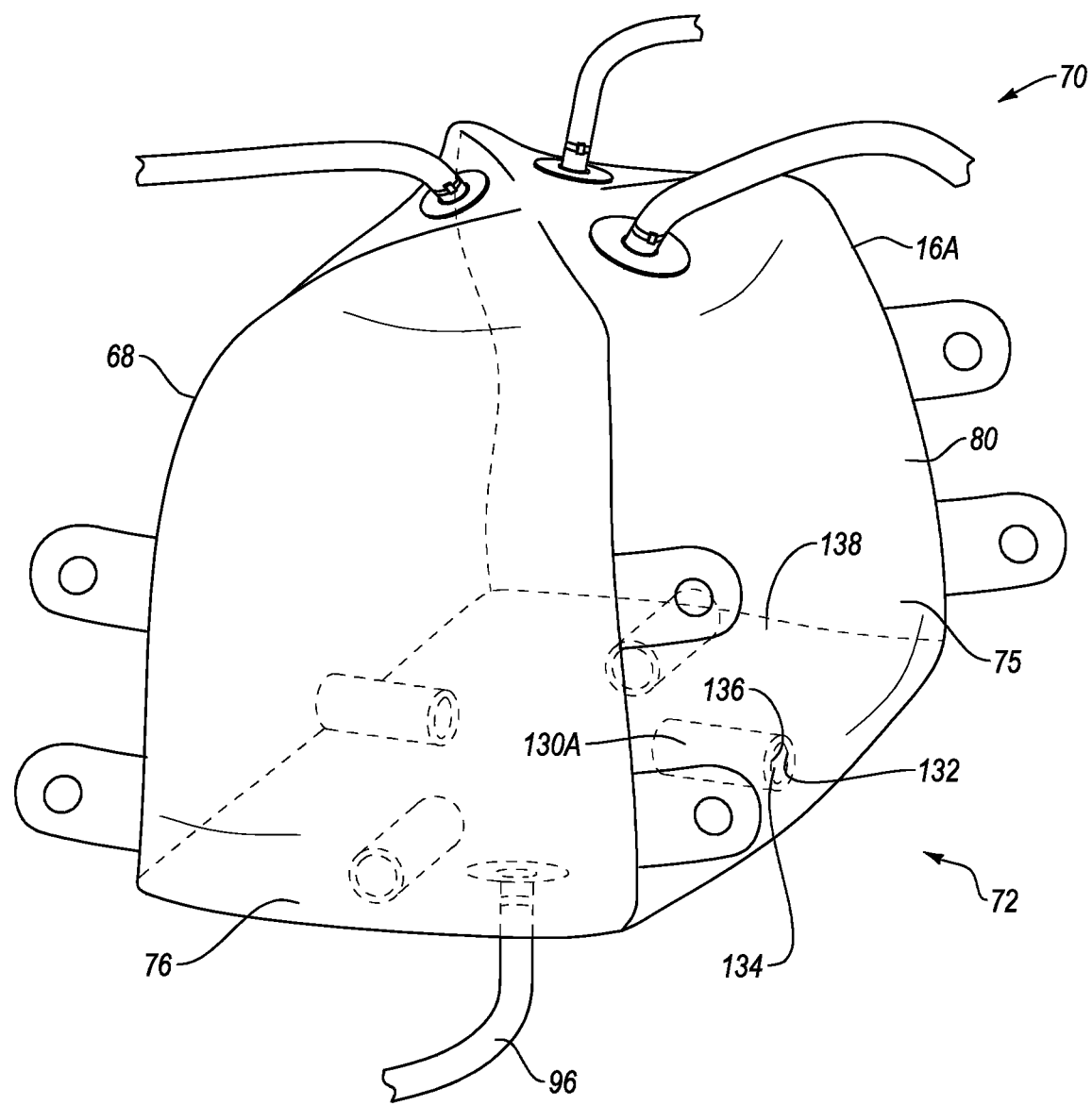
FIG. 9 is a perspective view of a container assembly shown in FIG. 6 having tubular baffles therein.

In one embodiment of the present invention, baffles can be used in association with the container assembly 16 to both improve mixing of the culture within compartment 80 and to improve mass transfer between culture 82 and the gas within container assembly 16. For example, depicted in FIG. 9 is container assembly 16A having baffles 130A disposed therein. In general, baffles 130 discussed herein are secured to flexible bag 68 at lower end 72 and more commonly on lower end wall 76. However, baffles 130 can also be mounted on sidewall 75. Baffles 130 can be attached by adhesive, welding, mechanical connection or using other conventional techniques. In the embodiment depicted, baffle 130A comprises a cylindrical tube having an interior surface 132 that bounds a passage 134 extending between opposing end faces 136 and 138. Although container assembly 16A is shown as having four baffles disposed within compartment 80, it is appreciated that one, two, three, five, six, seven, or more or at least each of the foregoing numbers of baffles can be used. In part, baffles 130 help to improve the mixing of culture 82 (FIG. 6) within flexible bag 68 as culture 82 is being moved by the movement of mixer table 12. Baffles 130 help to ensure that culture 82 is uniformly mixed and that the desired mass transfer between the gas and culture 82 is achieved.

Baffles 130 can be disposed randomly within compartment 80 or placed at predetermined locations. For example, in the embodiment depicted in FIG. 6, baffles 130 are positioned so that a central longitudinal axis of baffles 130 extends perpendicular to the adjacent side wall of flexible bag 86. This positioning helps to increase turbulent flow as the fluid flows over and around baffles 130. In other embodiments, the central longitudinal axis of baffles 130 can be disposed to form an inside angle with the adjacent sidewall of flexible bag 86 that is in a range between 45° and 90° and more commonly in a range between 60° and 90° or 75° and 90°. In another embodiment, baffles can be disposed so that a central longitudinal axis of each baffle 130 is disposed so as to be tangential to a common radius on lower end wall 76 of the flexible bag. The radius can be based on a point that is centrally located on lower end wall 76. For example, in the embodiment depicted in FIG. 10 and discussed below, the longitudinal axis of baffles 130B are disposed tangential to a radius R. This orientation helps to redirect fluid that is flowing out towards the sides of flexible bag 86. In other embodiments, baffles 130 need not be linear but can be curved, bent, or have an irregular pattern.

Figure 10:
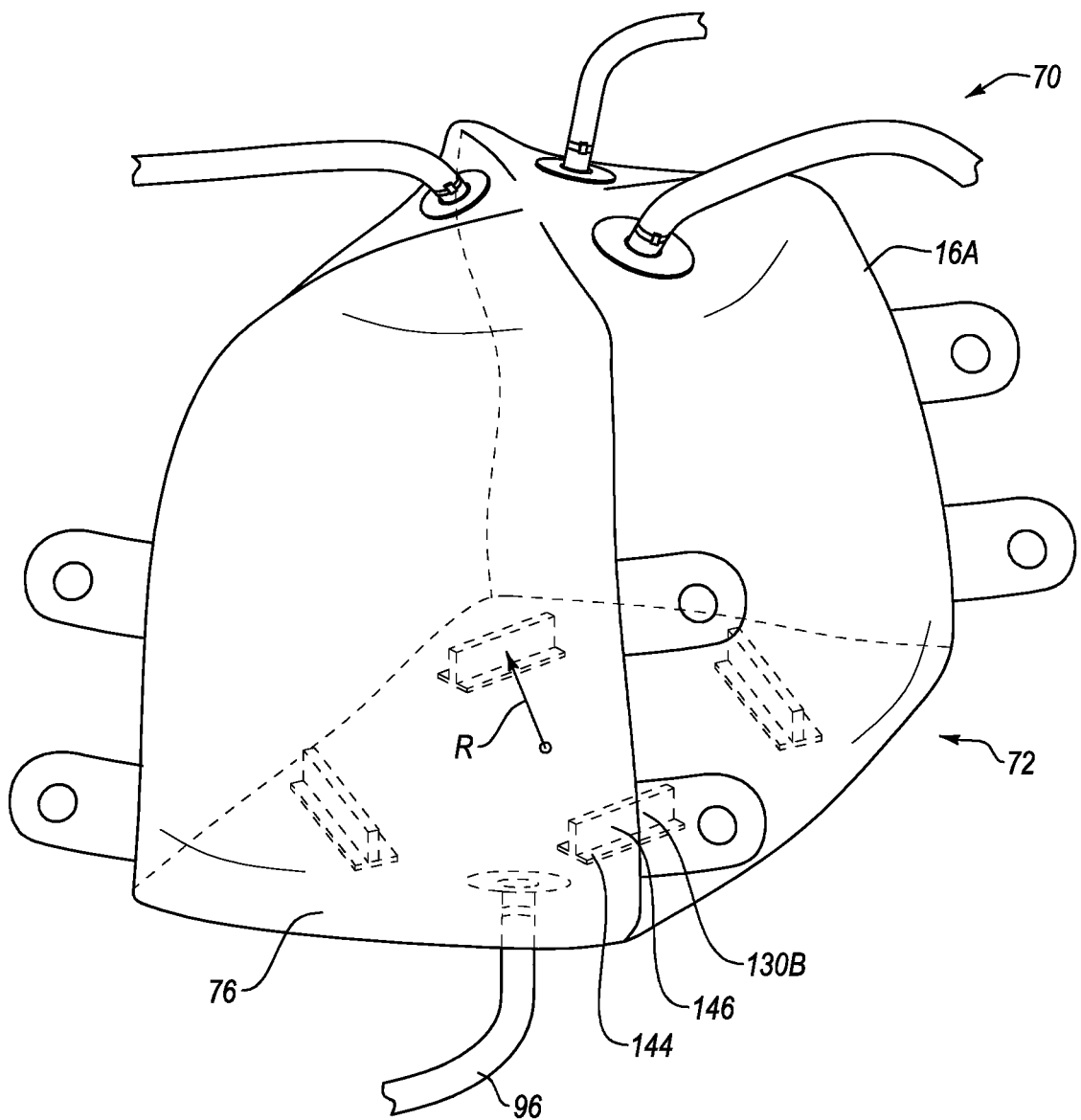
FIG. 10 is a perspective view of the container assembly shown in FIG. 6 having wall baffles therein.

As previously mentioned, it is appreciated that baffles 130 can be any desired configuration that will improve mixing of the culture. For example, depicted in FIG. 10 are baffles 130B disposed at lower end 72 or lower end wall 76 of a flexible bag 68. In contrast to baffles 130A, baffles 130B comprise a base 144 secured to flexible bag 68 in one or more of the manners previously discussed and a wall 146 upstanding therefrom. In the depicted embodiment, wall 146 has a rectangular configuration. In other embodiments, however, wall 146 could be square, semi-circular, polygonal, irregular, or any other desired configuration. Alternative embodiments as to numbers, positioning, use, and the like for baffle 130B are the same as previously discussed with regard to baffle 130A.

Figure 11:
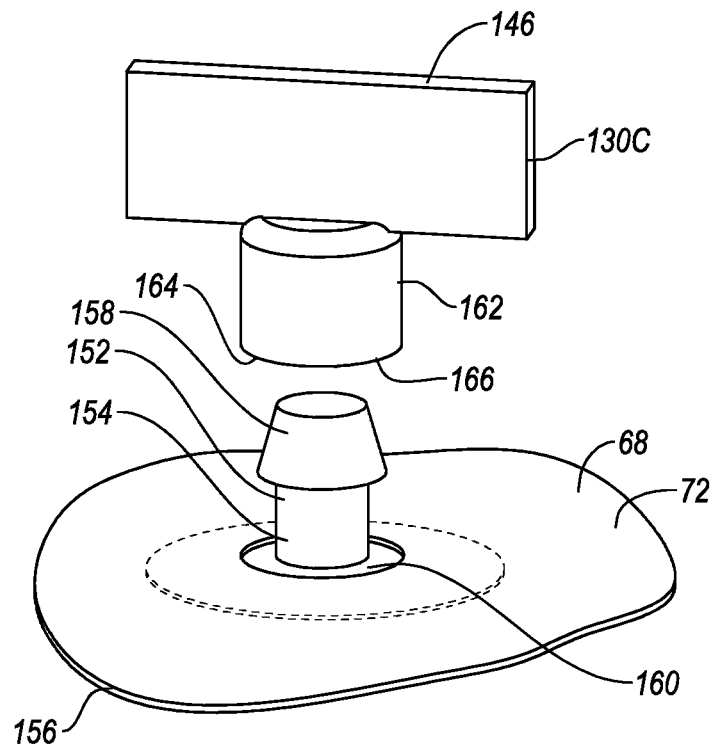
FIG. 11 is a perspective of a baffle which can be attached is a flexible bag by a fitting.

As previously mentioned, baffles 130 can be attached to flexible bag 68 using a variety of different techniques. In one embodiment, as depicted in FIG. 11, a fitting 152 is initially attached to flexible bag 68. Fitting 152 comprises an elongated stem 154, a flange 156 that encircles and radially outwardly projects from a first end of stem 154 and a tapered barb 158 that encircles and radially outwardly projects from the opposing end of stem 154. As with other conventional ports, fitting 152 can be attached to lower end wall 72 of flexible bag 68 by passing stem 152 through an opening 160 on lower end wall 72 and then welding or otherwise securing flange 56 to the bottom surface of the lower end wall 72. As a result, stem 154 upwardly projects into compartment 80 of flexible bag 68.

Figure 12:
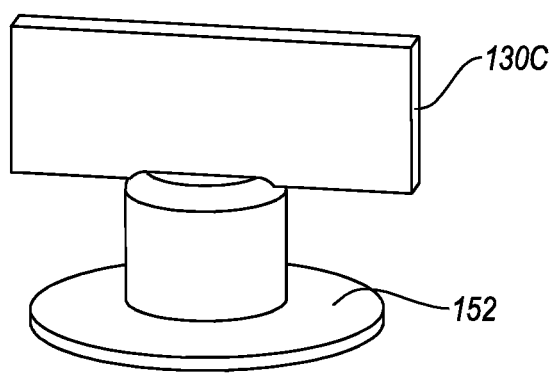
FIG. 12 is a perspective view of the assembled baffle and fitting shown in FIG. 11.

In this embodiment, a baffle 130C comprises a base 162 having a wall 146 upstanding therefrom. Base 162 comprises a collar having a bottom surface 164 with an opening 166 formed thereon. Opening 166 is configured to receive stem 154 and barb 158 in locking engagement. That is, barb 158 can form a friction fit within opening 166 or can engage with ribs or other features within opening 166 so that baffle 130C locks to fitting 152 as depicted in FIG. 12. Barb 158 is one example of a locking feature that can be formed on stem 152 for engaging base 162. In other embodiments, barb 158 can be replaced with other locking features such as ribs, knobs, catches, and other projections that extend from stem 154 and engage base 162.

Figure 13:
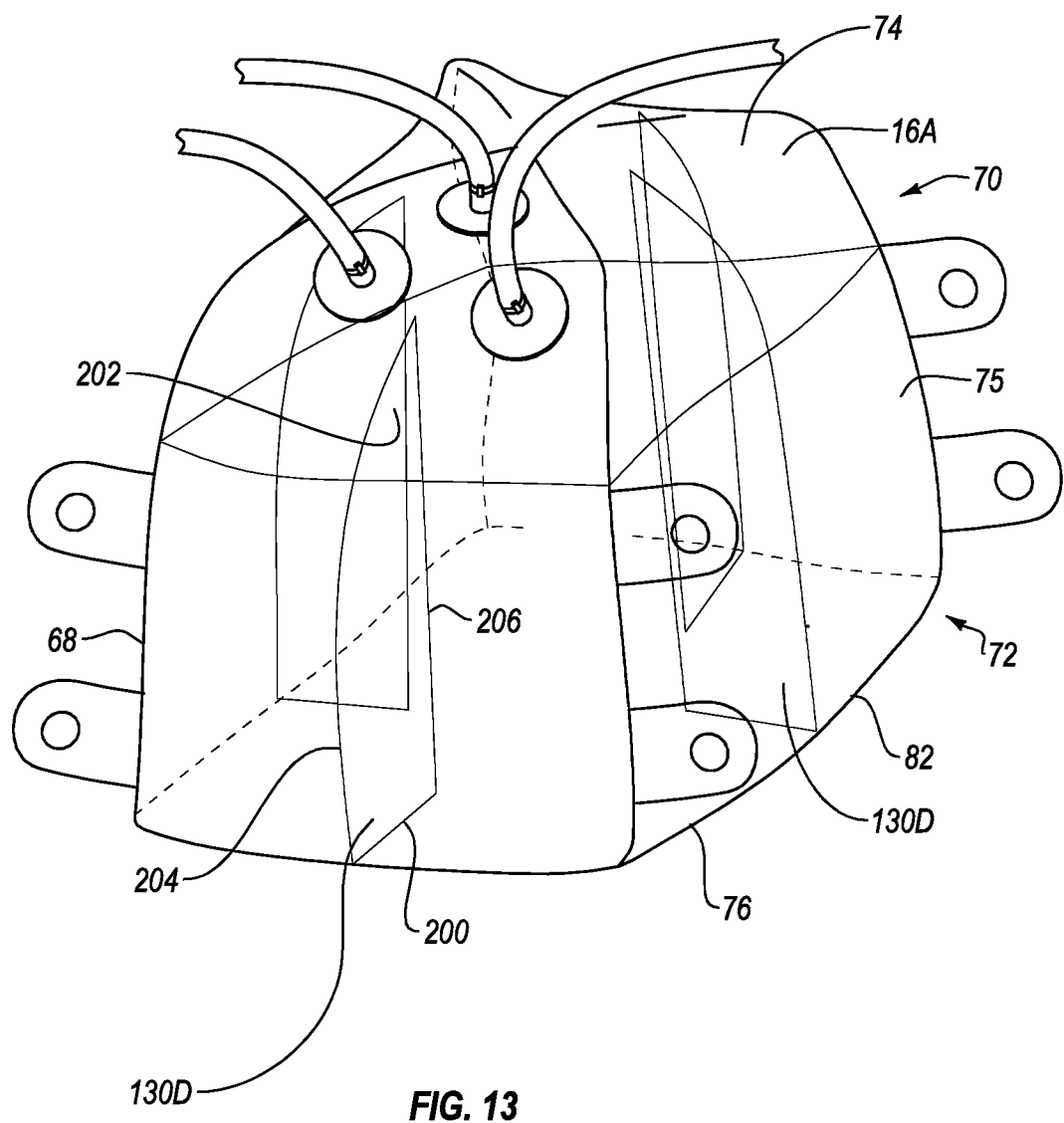
FIG. 13 is a perspective view of an alternative container assembly having film baffles.

Depicted in FIG. 13 is another embodiment on container assembly 16A having flexible baffles 130D disposed therein. Each baffle 130D comprise a sheet of polymeric film, such as the same film used to make flexible bag 68 or film consisting of just one material such as HDPE (high-density polyethylene). Each baffle 130D has a lower end 200 secured to lower end wall 76, an upper end 202 secured to upper end wall 74, an outside edge 204 secured to sidewall 75, and an inside edge 206 that is freely disposed within compartment 80 of flexible bag 68. Baffles 130D can be secured to flexible bag 68 by welding, adhesive, or the like. As platform 20 (FIG. 1) is moved, baffles 130D help to uniformly mix culture 82 within compartment 80.

Figure 14:
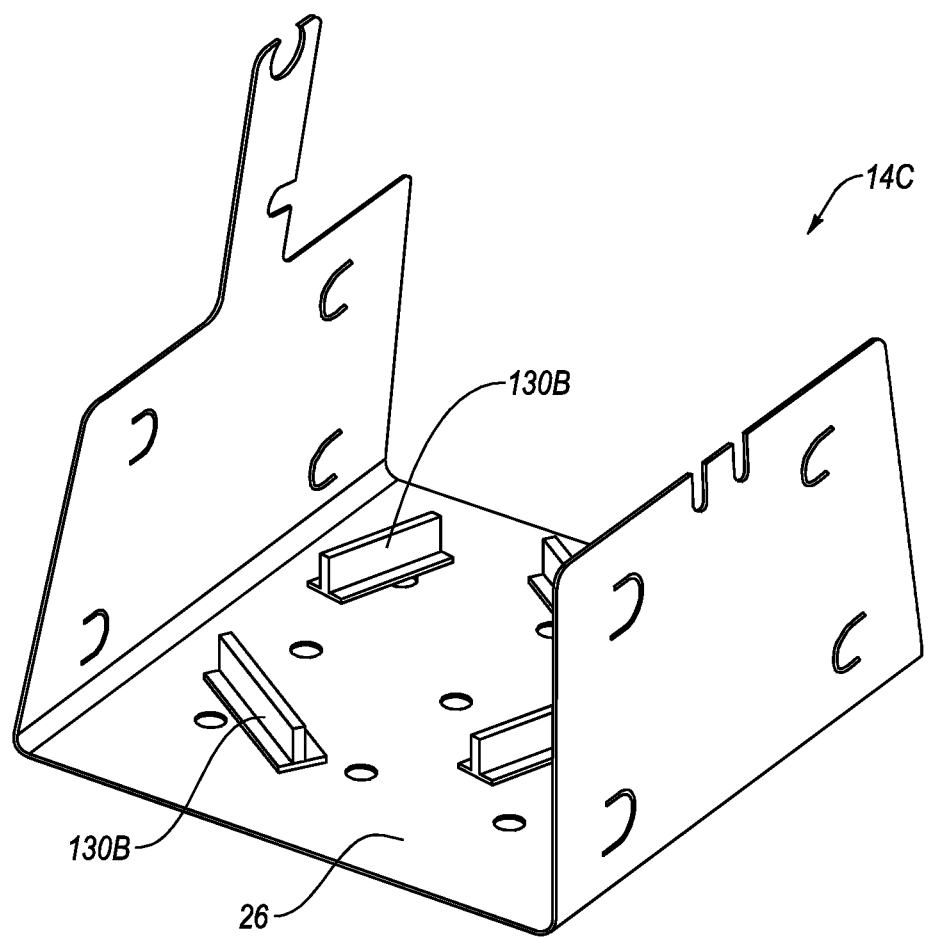
FIG. 14 is a perspective view of a retainer having baffles mounted directly onto the floor of the retainer.

In contrast to positioning baffles 130 within compartment 80 of flexible bag 68, baffles 130 can also be secured to floor 26 of retainer 14 or directly onto platform 20 of mixer table 12 so that once container assembly 16 is received within chamber 40 of retainer 14, flexible bag 68 sits on top of baffles 130. For example, as depicted in FIG. 14, baffles 130B are disposed on floor 26 of retainer 14C. Again, baffles 130 can be a variety of different configurations and can be used in a variety of different numbers and different orientations, each as discussed above. As a result of flexible bag 68 sitting on baffles 130B, lower end wall 76 flexes up over top of baffles 130B, thereby effectively functioning as baffles within flexible bag 68. It is appreciated that baffles 130 can be located on any of the floors 26 previously discussed with regard to retainers 14 or can be mounted directly onto platform 20 between the retainer walls as depicted in FIG. 5.

Figure 15:
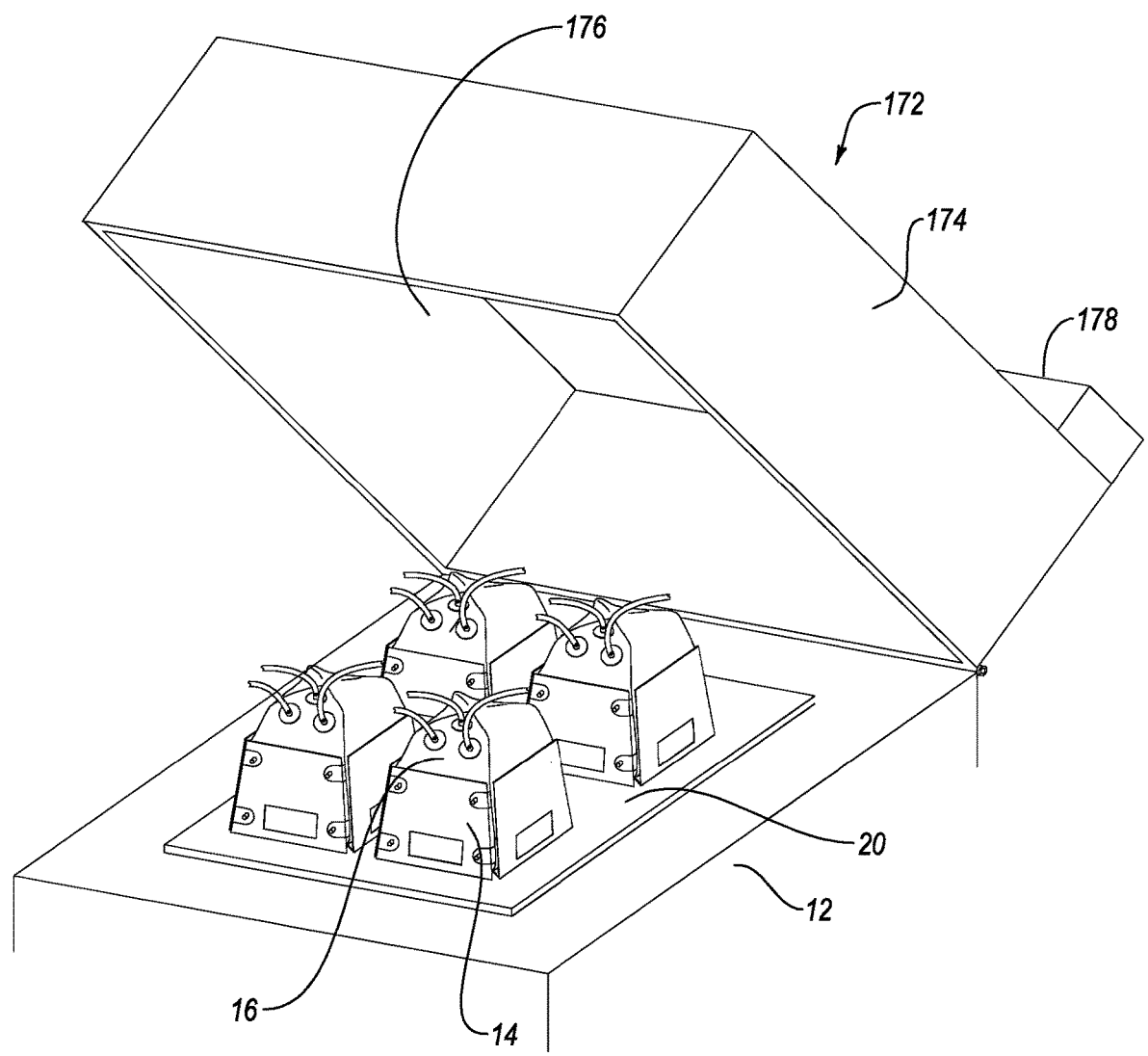
FIG. 15 is a perspective view of the mixer table shown in FIG. 1 having a plurality of retainers and container assemblies mounted thereon and an incubator coupled thereto.

As depicted in FIG. 15, because container assemblies 16 are relatively small, it is appreciated that a plurality of different retainers 14 and corresponding container assemblies 16 can be simultaneously mounted on platform 20 of mixer table 12. Each container assembly 16 can then concurrently culture a separate culture therein. In the depicted embodiment, four retainers 14 and four corresponding container assemblies 16 are disposed on platform 20. In other embodiments, 2, 3, 5, 6, 7 or more or at least each of the foregoing numbers of retainers 14 and container assemblies 16 can be disposed on platform 20 for concurrently culturing a separate culture.

FIG. 15 also shows that an incubator 172 can operate with mixer table 12 for controlling the temperature of culture 82 within container assemblies 16. Incubator 172 comprises a hood 174 that bounds an enclosure 176 and a temperature regulating source 178 for heating and/or cool enclosure 176 or items within the enclosure 176. Temperature regulating source 178 can comprise a radiant heat source, heated forced air, electrical heating element, a heated fluid system or any other type of heating system that can be used to warm culture 82 within container assembly 16. Typically, heat source 178 will warm the air within enclosure 176 which will in turn warm culture 82. Temperature regulating source 178 can also comprise an air conditioner, a chilled fluid system, heat sink or other systems that can be used to cool culture 82 within container assembly 16. The cooling is typically accomplished by cooling the air within enclosure 176.

Hood 174 can be hingedly mounted or otherwise movably mounted to mixer table 12 so that it can be moved from an open position wherein container assemblies 16 can be accessed and a closed position wherein hood 174 covers retainers 14 and container assemblies 16. When in the closed position, a controller coupled with temperature regulating source 178 can be used to regulate the temperature within enclosure 176.

During one typical method of operation, the desired number of retainers 14 are mounted on platform 20 of mixer table 12 following of which a container assembly 16 is received within chamber 40 of each retainer 14 and is secured to each retainer 14. A growth media is dispensed into each container assembly 16 through a tube 88. A gas is also delivered into each container assembly 16 through a tube 88 so as to fill head space 84. Hood 174 is typically closed and incubator 172 is used to warm the growth media to the desired temperature. Where desired, the growth media and/or gas can be delivered into container assembly 16 prior to positioning container assembly 16 within chamber 40. Once the desired temperature is reached, the starter culture is dispensed into the growth media of each container assembly 16. Mixer table 12 is activated so that platform 20 moves, thereby mixing the culture within each container assembly 16 so that the culture is continuously uniformly mixed and so that the culture is sufficiently oxygenated through mass transfer with the gas in head space 84.

The culture is allowed to grow under these conditions until a predetermined condition is met. For example, the culture may be allowed to grown for a predetermined period of time or the culture may be allowed to grown until a predetermined cell/microorganism density is achieved. The density can be determined by periodically taking a sample of the culture from each container assembly, such as by using one of methods previously discussed, and testing the sample. For example, the sample can be extracted out through a tube 88 at the upper end or side of container assembly 16 or through a tube 96 at the lower end of container assembly 16. In one method, the sample is taken by first removing container assembly 16 from retainer 14. Container assembly 16 can then be manually placed within a sterile hood and/or inverted following which the sample is dispend or drawn from of container assembly 16. Container assembly 16 is then returned to retainer 14 for further processing. In other embodiments, the sample can be drawn from container assembly 16 while container assembly 16 remains resting on platform 20. In this embodiment, mixer table 12 can be deactivated prior to taking the same and then reactivated after the sample has been taken.

The sample can also be tested to determine the other physical and/or chemical properties discussed herein. Based on the results of such testing, needed components can be added to the culture or the operating conditions, such as temperature, rate of mixing or gas content, can be altered. In contrast to or in addition to taking samples, sensors can be mounted on or otherwise associated with container assembly 16 for continuously monitoring the various or select chemical and/or physical properties of the culture.

Based on the volumes and conditions discussed herein, culture 82 comprising a microbial culture will typically be grown in container assembly 16 for a period of time ranging from about 1 hour to about 48 hours with about 4 hours to about 24 hours or about 4 hours to about 16 hours or about 4 hours to about 8 hours being more common before reaching the desired density. For mammalian or insect cell culture, culture 82 will typically be grown in container assembly 16 for a period of time ranging from about 1 day to about 14 days with about 2 days to about 3 days or about 3 days to about 5 days being more common before reaching the desired cell culture density. Longer culture times may be achieved with a nutrient feed. Culture 82 may be both fully grown and removed from container assembly 16, such as by being transferred to another container, with in the above time periods. Other time periods can also be used.

Once the predetermined condition is satisfied, mixer table 12 is turned off. Each container assembly 16 can then be manually removed from the corresponding retainer 14 and then coupled to a secondary container through one of tubes 88. Where further processing is desired, the secondary container is typically larger than container assembly 16/flexible bag 68 and forms a portion of a bioreactor or fermenter. Culture 82 from container assembly 16 can then be dispensed, such as through gravity flow or pumping, into the secondary container through a tube 88 or 96. Where needed, container assembly 16 can be inverted prior to dispensing. Container assembly 16 can then be discarded and the process repeated. Other alternative embodiments and steps for the present invention can also be performed as previously discussed herein.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for culturing a microbial or cellular seed culture comprising:
   positioning a flexible first bag within a chamber of a first retainer, the first retainer having an interior surface at least partially bounding the chamber and an opposing exterior surface, the first retainer being secured to a movable platform;
   producing a suspension within a compartment of the first bag, the suspension comprising a growth media and a microbial or cellular starter culture combined therewith;
   securing a first tab projecting from the first bag to a first fastener disposed on the exterior surface of the first retainer, wherein the first tab is a flexible polymeric film; and
   moving the platform so that the suspension is mixed within the compartment of the first bag while microorganisms or cells of the starter culture grow, the suspension having a maximum volume of less than 10 liters.

2. The method as recited in claim 1, wherein the first retainer comprises two sidewalls upstanding from the platform with a slot being formed therebetween, the step of securing comprising:
   passing the first tab projecting from the first bag through the slot; and
   securing the first tab to the first fastener.

3. The method as recited in claim 1, further comprising securing a second tab projecting from the first bag to a second fastener disposed on the exterior surface of the first retainer.

4. The method as recited in claim 3, wherein the first tab projects from an upper end of the first bag and the second tab projects from a lower end of the first bag so that the first tab and the second tab are disposed at different elevations when secured to the first fastener and the second fastener, respectively.

5. The method as recited in claim 1, wherein the step of moving the platform comprises continuously moving the platform horizontally within a single plane.

6. The method as recited in claim 1, further comprising:
   positioning a flexible second bag within a chamber of a second retainer, the second retainer being secured to the platform; and
   producing a suspension comprised of a growth media and a microbial or cellular starter culture within a compartment of the second bag so that when the platform is moved, the suspensions are concurrently mixed within the first bag and the second bag.

7. The method as recited in claim 1, further comprising not measuring a pH or a dissolved oxygen content of the suspension while the suspension is within the compartment of the first bag during the entire time that the suspension is within the compartment of the first bag.

8. The method as recited in claim 1, further comprising either not supplying a forced flow of gas into the compartment of the first bag during an entire time the suspension is being grown therein or supplying a forced flow of gas into the compartment of the first bag during less than 10% of a total time period that the suspension is being grown within compartment of the first bag.

9. The method as recited in claim 1, further comprising growing and removing the suspension from the compartment of the first bag within a period of time in a range between 1 hour and 24 hours.

10. A method for culturing a microbial or cellular seed culture comprising:
- positioning a flexible first bag within a chamber of a first retainer, the first retainer having an interior surface at least partially bounding the chamber and an opposing exterior surface, the first retainer being secured to a movable platform;
- securing a first tab projecting from the flexible first bag to a first fastener disposed on the exterior surface of the first retainer, wherein the first tab is a flexible polymeric film;
- producing a suspension within a compartment of the first bag, the suspension comprising a growth media and a microbial or cellular starter culture combined therewith;
- moving the platform so that the suspension is mixed within the compartment of the first bag while microorganisms or cells of the starter culture grow, the suspension having a maximum volume of less than 10 liters;
- removing the first bag from the first retainer after partial growth of the microorganisms or cells;
- taking a sample of the suspension from the first bag while the first bag is removed from the first retainer, wherein the step of taking the sample comprises at least partially inverting the first bag while taking the sample; and
- returning the first bag to the chamber of the first retainer for further growth of the microorganisms or cells.

11. The method as recited in claim 10, wherein the compartment of the first bag is free of any movable mixing element.

12. The method as recited in claim 10, wherein the suspension has a maximum volume of less than 3 liters.

13. The method as recited in claim 10, wherein after the step of returning the bag to the chamber of a first retainer, transferring the suspension within the first bag to a container that is larger than the first bag and further growing the microorganisms or cells within the container.

14. The method as recited in claim 10, wherein the first bag is void of any sensors disposed thereon during growth of the microorganisms or cells therein.

15. A method for culturing a microbial or cellular seed culture comprising:
- positioning a flexible first bag within a chamber of a first retainer, the first retainer having an interior surface at least partially bounding the chamber and an opposing exterior surface, the first retainer having an upstanding sidewall that is reclined toward the chamber at an angle in a range between 2° and 15°, the first retainer being secured to a movable platform;
- producing a suspension within a compartment of the first bag, the suspension comprising a growth media and a microbial or cellular starter culture combined therewith; and
- moving the platform so that the suspension is mixed within the compartment of the first bag while microorganisms or cells of the starter culture grow, the suspension having a maximum volume of less than 10 liters; and
- securing a first tab projecting from the first bag to a first fastener disposed on the exterior surface of the first retainer,
- wherein the first retainer comprises two sidewalls upstanding from the platform with a slot being formed therebetween, the step of securing comprising:
  - passing the first tab projecting from the first bag through the slot; and
  - securing the first tab to the first fastener.

16. The method as recited in claim 15, wherein the step of moving the platform comprises continuously moving the platform horizontally within a single plane.

17. The method as recited in claim 15, wherein no movable mixing elements are disposed within the compartment of the first bag.

* * * * *